United States Patent [19]

Sloma et al.

[11] Patent Number: 5,891,701
[45] Date of Patent: Apr. 6, 1999

[54] NUCLEIC ACIDS ENCODING A POLYPEPTIDE HAVING PROTEASE ACTIVITY

[75] Inventors: Alan Sloma; Lynne Christianson, both of Davis, Calif.

[73] Assignee: Novo Nordisk BioTech Inc., Davis, Calif.

[21] Appl. No.: 873,479

[22] Filed: Jun. 12, 1997

[51] Int. Cl.$^6$ ............................. C12N 1/00; C12N 1/21; C12N 9/54; C12N 15/57; C12N 15/63

[52] U.S. Cl. ..................... 435/221; 435/220; 435/320.1; 435/252.3; 435/252.31; 435/252.33; 435/252.34; 435/252.35; 435/254.11; 435/832; 536/23.2

[58] Field of Search ..................................... 435/221, 220, 435/832, 325, 410, 320.1, 252.3, 254.11, 252.31, 252.33, 252.34, 252.35; 536/23.2

[56] References Cited

FOREIGN PATENT DOCUMENTS 404197182  7/1992  Japan .

*Primary Examiner*—Robert A. Wax
*Assistant Examiner*—Gabriele E. Bugaisky
*Attorney, Agent, or Firm*—Steve T. Zelson; Carol E. Rozek; Robert L. Starnes

[57] ABSTRACT

The present invention relates to isolated nucleic acid sequences encoding polypeptides having protease activity, in which the polypeptides are obtainable from an alkalophilic Bacillus species having enhanced stability towards bleaching agents of the peroxy type. The invention also relates to nucleic acid constructs, vectors, and host cells comprising the nucleic acid sequences as well as recombinant methods for producing the polypeptides.

21 Claims, 11 Drawing Sheets

FIG. 5A

```
CTTAGGCAAGCTTTACTCTATACAGAGATTACATCCTCAAGCCATTGAAGAATTCGAAAAAGTTATTATTTAAA     75
AGAGGATAGGGGTTAGACAGTAAATTAAATTCGATTTATTGTCTTTTGATGGAATACGATAACATGGAAGATTC    150
TACTCAATGTAGAAAATGGTTAGAAATCTTTGCTAACTAGTCCAGACGAATTGGTAGAATATCATTA           225
TTATTTCACCATTTTTGACTATGTCCTAGCAGACAATATGGAGCTTGATGTCTATTCCAAGAAGTCGTTTT      300
ACCTTTTTCAACAACAAAAAAGCTATTAAAAGAACCAATTATTAAATATGCAGAGAAATAAAGAACAAACTTTTATA 375
TTGTTATATAATACAAAAAAAGCTACTATTCGTTTATGCTACCAAGAACTACTATTCTTTTTTAGTAGTACTTT   450
CTAAGGGGAGGGTAATATGAAAAAAAAGCCTCAAGTAATTGCACATGGCGAGGTTACTGCTTTAAAAGATGAACATCCTGAGCC 525
GGAAAAATCTATTCAAGAGCCTCAAGTAATTGCACATGGCGAGGTTACTGCTTTAAAAGATGAACATCCTGAGCC   600
GCTTCCAAATGGTCGCTGTAGTCGCTTGACAGTAATTTCTCTGGAGAGGGTTCTTTTTCATTTTTTAGAA        675
AATATTGAATGGTCGCTGTAGTCTGGCTTGACAGTAATTTCCATTGGGAAAGTATGAGCCCAAAAAGCGAATTA    750
TGAAGCTATTTTAATCTGAATTTCCCAATATAAAGTTTTTGTTTCCTGTGATAATTAATGATGTGTTATAAAT    825
TGAGAGGAGTTGAGCTATAGAATGAGAAAGAAAGGATCGAAGAGGTTTTTATCCGTTTTATCAGTTGCTGCA      900
                           M  R  K  K  G  S  K  R  V  F  L  S  V  A  A
CTATTGTCTTCTGTTGCTTAAGCAGTCCTTCTACTATTGGGGCGAACAATTTGAATTGGACTTTAAGGGGATA    975
 L  L  S  S  V  A  L  S  S  P  S  T  I  G  A  N  F  E  L  D  F  K  G  I
GAGACACTTACGCTAGAGAGAAGGCTGCCACCAAGGAAAACGGGAAAGGCATCTTTTCTTGTAAACTCTGAA   1050
 E  T  L  L  E  K  A  A  T  K  Q  G  K  A  S  F  L  V  N  S  E
AATGTGAAAATCCCAAAGAGTATTCAAAGAGAAACTAGAAACTTCAACTAGTTCCAGCGGATAACAAGCTATATATCGTTCAA 1125
 N  V  K  I  P  K  S  I  Q  K  L  E  V  P  A  D  N  K  L  Y  I  V  Q
TTTGACGGACCTATTTTAGAGGAAACGCAACTTCAACTAGAAGAAGACGGAGCGAAAATTCTCGATTACATACCA 1200
 F  D  G  P  I  L  E  E  T  Q  L  Q  L  E  K  T  G  A  K  I  L  D  Y  I  P
GATTACGCTTATATTGTCGAATATGATGGGGATGTAAAGGCCGTAACTAACGCAATTGCGCATTTGGAATCGGTT 1275
 D  Y  A  Y  I  V  E  Y  D  G  D  V  K  A  V  T  N  A  I  A  H  L  E  S  V
GAACCATATTTACCTTTATATATAAATAGACCCGCAATTATTTCCAGAGGAGCTTCTGAATTAGTAGAAACAGTA 1350
```

FIG. 5B

```
      E   P   Y   L   P   L   Y   K   I   D   P   Q   L   F   S   R   G   A   S   E   L   V   E   T   V
GCTTTAGATAAAAAGCAAAGAAGTAAAGAAGAGTACGTTTAAGAGGATTGGAACAAATTGCCAATACGGCGACAAAT  1425
      A   L   D   K   K   Q   R   S   K   E   V   R   L   R   G   L   E   Q   I   A   Q   Y   A   T   N
AATGATGTATTATACGTAACCCCAAAGCCTGAATACGAAGTTTTGAATGACGTGGCCCGTGGCATTGTGAAAGCA  1500
      N   D   V   L   Y   V   T   P   K   P   E   Y   E   V   L   N   D   V   A   R   G   I   V   K   A
GACGTCGCACAAATAACTTTGGCTTATATGGACAAGGACAGATTGCTGATACTGGGCTTGATACA  1575
      D   V   A   Q   N   F   G   L   Y   G   Q   Q   I   V   A   V   A   D   T   G   L   D   T
GGAAGAAATGACAGTTCGATGCATGAAGCATTCCGCGTAAGATTACCGCACTATATGCACTGGGCAGAACGAAT  1650
      G   R   N   D   S   M   H   E   A   F   R   G   K   I   T   A   L   Y   A   L   G   R   T   N
AACGCCAATGATCCAAATGGAACCCATGTTGCTGGATCTGTGTTAGGAAATGCTACAAATAAAGGGATG  1725
      N   A   N   D   P   N   G   H   G   T   H   V   A   G   S   V   L   G   N   A   T   N   K   G   M
GCACCGCAAGCCAATTATTCAGTCAAGACTCTCGAAATCTAGTCTTTCAATCTATTATGGATGGTGGGGGACTACCTGCTAATCTA  1800
      A   P   Q   A   N   L   V   F   Q   S   I   M   D   S   G   G   G   L   P   A   N   L
CAAACATTATTCAGTCAAGACTCTCGAAATCTAGTCTTTCAATCTATTATGGATAGTGGTGGGGGACTACCTGCTAATCTA  1800
      Q   T   L   F   S   Q   A   Y   S   A   G   A   R   I   H   T   N   S   W   G   A   P   V   N   G
GCCTATACGACAGACTCTCGAAGCGGTAGCACAATCAGTCAGTGCACCAGGAACAGCAACAAAAATGCGATTACAGTTGGGCAACCGAA  2025
      A   Y   T   T   D   S   R   N   V   D   D   Y   V   R   K   N   D   M   T   I   L   F   A   A   G
AATGAGGAGGACCAGGTAGCGGTACAATCAGTCAGTGCACCAGGAACAGCAACAAAAATGCGATTACAGTTGGGCAACCGAA  2025
      N   E   G   P   G   S   G   T   I   S   A   P   G   T   A   K   N   A   I   T   V   G   A   T   E
AACCTACGTCCAAGCTTCGGATCTTATGCGGATAATATTAACCATGTTGCTCAATTCTCTTCACGAGGTCCTACT  2100
      N   L   R   P   S   F   G   S   Y   A   D   N   I   N   H   V   A   Q   F   S   S   R   G   P   T
AGAGATGGAGGACGTATTAAGCCGGACGTCATGGACGTATATTCTCTGCTAGATCATCATTAGCTCCA  2175
      R   D   G   R   I   K   P   D   V   M   A   P   G   T   Y   I   L   S   A   R   S   L   A   P
GATTCCTCATTCTGGGCAAACCATGATAGTAAAATATGCCTACTTCTATGGCTGGTGGTACTCCAATTGTA  2250
      D   S   S   F   W   A   N   H   D   S   K   Y   A   Y   M   G   G   T   S   M   A   T   P   I   V
```

FIG.5C

```
GCAGGTAATGTTGCACAATTAAGGGAGCATTTTGTGAAAAATAGAGGGGTAACTCCTAAGCCTTCCCTTTTAAAA  2325
  A  G  N  V  A  Q  L  R  E  H  F  V  K  N  R  G  V  T  P  K  P  S  L  L  K
GCTGCTTTAATTGCAGGTGCTGCGGATGTTGGACTTGGCTTTCCAAATGGTAACCAAGGATGGGGAAGAGTAACG  2400
  A  A  L  I  A  G  A  A  D  V  G  L  G  F  P  N  G  N  Q  G  W  G  R  V  T
TTAGATAAATCCCTAAATGTCGCATTTGTGAATGAAACGAGCCCTTTATCAACAAGTCAAAAAGCAACATATTCG  2475
  L  D  K  S  L  N  V  A  F  V  N  E  T  S  P  L  S  T  S  Q  K  A  T  Y  S
TTTACGGCTCAAGGTAAACCCTTAAAAATATCACTTGTTGGTCAGATGCACCAGGTAGCACGACGGCATCA  2550
  F  T  A  Q  G  K  P  L  K  I  S  L  V  W  S  D  A  P  G  S  T  T  A  S
CTAACTTAGTGAATGATTAGTAATCACTGCACCAAATGGAACTAAATACGTCGGAAATGACTTTACA  2625
  L  T  L  V  N  D  L  V  I  T  A  P  N  G  T  K  Y  V  G  N  D  F  T
GCACCGTATGATAACAATTGGGATGGCAGAAACAACGTGGAAAATGTGTTTATCAATGCTCCTCAAAGCGGAACG  2700
  A  P  Y  D  N  N  W  D  G  R  N  N  V  E  N  V  F  I  N  A  P  Q  S  G  T
TATACAGTCGAAGTGCAGGCTTACAATGTACCAGTAAGTCCGCAAACCTTTTCTTTAGCGTACATTAAAAT  2775
  Y  T  V  E  V  Q  A  Y  N  V  P  V  S  P  Q  T  F  S  L  A  I  V  H
ATTGGAAGGAGAGTTGTTGATGAATATCAGCAGCTCTTTTTCGTAAAGGTTGTTGC  2850
TTTAAGTCGGTAAAAAGTCGGTATTTGGACTTTTTACCAGTCATTTTGCTTGGGAAATTGATGAGAGTACTTTCA  2925
TTTACTGATGGAAAAGAGCACGATTGCAACGTTTATGACGGGGTGATTTCTATTTCGAAAAGCAACAAAGTATGC  3000
GAAA  3004
```

FIG. 6A

JP170 vs. subtilisin

```
  1   MRKKGSKRVFLSVLSVAALLSSVALSSPSTIGANNFELDFKGIETLTLEKAATKQG

57   KTGKASFLVNSENVKIPKSIQKKLEVVPADNKLYIVQFDGPILEETQLQLEKTGAK
  1                                           MKRSGKIFTTAMLAVTLM

113   ILDYIPDYAYIVEYDGDVKAVTNAIAHLESVEPYLPLYKIDPQLFSRGASELVETV
 20   MPAIGVSANRGNAADGNEKFRVLVDSANQNNLKNVKEQYGVHWDFAGEGFTTNMNE

169   ALDKKQRSKEVRLRGLEQIAQYATNNDVLYVTPKPEYEVLNDVARGIVKADVAQNN
 76   KQFNALQNNKNLTVEKVPELEIATATNKPEALYNAMAASQSTPWGIKAIYNNSNLT

225   FGLYGQGQIVAVADTGLDTGRNDSSMHEAFRGKITALYALGRTNNANDPNGHGTHV
      |-|--+||-|||++|++-|-|-+++-+-|---++-+----|+++|-+||||||
132   STSGGAGINIAVLDTGVNTNHPDLS.NNVEQCKDFTVGTNFTDNSCTDRQGHGTHV

281   AGSVLGN.AT.N..KGMAPQANL.VFQSIMDSGGGLG.GLPANLQTLFSQAYSAGA
      |||+|+|-+|-+---|+||+|+|-+++-+-|+|+|-+---+---++---+||-+-++
187   AGSALANGGTGSGVYGVAPEADLWAYKVLGDDGSYADDIAEAIRHAGDQATALNT

331   RIHTN.SWGAPVNGAYTTDSRNVDDYVRKNDMTILFAAGNEGPGSGTISAPGTAKN
      ++--|-|-|+---++-|++--|-||+---+-+-|+-|||+||--|+|+-||+--|
243   KVVINMSLGSSGESSLITNA..V.DYAYDKGVLIIAAAGNSGPKPGSIGYPGALVN

386   AITVGATENLRPSFGSYADNINHVAQFSSRGPTRDGRIKPDVMAPGTYILSARSSL
      |++|+|-||---+-|+|------+||+||||||--|-------|+--|---+||--+-
296   AVAVAALENTIQN.GTY.....RVADFSSRGHKR..TAGDYVIQKGDVEISA.PGA

442   APDSSFWANHDSKYAYMGGTSMATPIVAGNVAQLREHFVKNRGVTPKPSLLKAALI
      |---|-|---|+-||-++|||||+|-+||-+|++
343   AV.YSTW..FDGGYATISGTSMASPHAAGLAAKIWAQSPAASNVDVRGELQTRASV

498   AGAADVGLGFPNGNQGWGRVTLDKSLNVAFVNETSPLSTSQKATYSFTAQAGKPLK
396   NDILSGNSAGSGDDIASGFGFAKVQ

554   ISLVWSDAPGSTTASLTLVNDLDLVITAPNGTKYVGNDFTAPYDNNWDGRNNVENV

610   FINAPQSGTYTVEVQAYNVPVSPQTFSLAIVH
```

```
  1  MRKKGSKRVFLSVLSVAALLSSVALSSPSTIGANNFELDFKGIETLTLEKAAT
     ||+|||-|||++-||+|+||-+|||-|-||-+|+++|+|+++|--+-+-+
  1  MKGKKRVVLSVVASAAILASVMVSSP.TSGA.DFQVNFNGVKSLE.NASLV

54  KQGKTGKASFLVNSENVKIPKSIQKKLEVVPADNKLYIVQFDGPILEETQLQL
     |--++|+||||++||++|||+||||||+|--||+|||||-|||-||-+--|
 50  KPISSGEASFLVDTENINIPKGIQKKLEAVQKDNELYIVQFTGPISEEERKGL

107  EKTGAKILDYIPDYAYIVEYDGDVKAVTNAIAHLESVEPYLPLYKIDPQLFSR
     |+-|++||||+||||+||+|-+|-++-++---+|+|+|+|||||||+|+++
103  ESLGVSILDYVPDYAFIVQYSGATKNIS.TLHSVENVQPFLPLYKIDPELLTK

160  GASELVETVALDKKQRSKEVRLRGLEQIAQYATNNDVLYVTPKPEYEVLNDVA
     |||+||++|-|+-|+++|++++-||++|+|||+|||||||++||||||++||||
155  GASQLVQAVILNTKHENKNMKFTGLDEIVQYAANNDVLYISPKPEYELMNDVA

213  RGIVKADVAQNNFGLYGQGQIVAVADTGLDTGRNDSSMHEAFRGKITALYALG
     ||||||||||||+|||||||+|||||||||||||||||||||||||||||||
208  RGIVKADVAQNNYGLYGQGQLVAVADTGLDTGRNDSSMHEAFRGKITALYALG

266  RTNNANDPNGHGTHVAGSVLGNATNKGMAPQANLVFQSIMDSCGGLGGLPANL
     |||||+|||||||||||||||||-||||||||||||||||+||||||||+||
261  RTNNASDPNGHGTHVAGSVLGNALNKGMAPQANLVFQSIMDSSGGLGGLPSNL

319  QTLFSQAYSAGARIHTNSWGAPVNGAYTTDSRNVDDYVRKNDMTILFAAGNEG
     +||||||++|||||||||||||||||||++|+|+|||+|||+||||||||
314  NTLFSQAWNAGARIHTNSWGAPVNGAYTANSRQVDEYVRNNDMTVLFAAGNEG

372  PGSGTISAPGTAKNAITVGATENLRPSFGSYADNINHVAQFSSRGPTRDGRIK
     |+|||||||||||||||||||||-||||||-|||-||+||||||-|||||||
367  PNSGTISAPGTAKNAITVGATENYRPSFGSIADNPNHIAQFSSRGATRDGRIK

425  PDVMAPGTYILSARSSLAPDSSFWANHDSKYAYMGGTSMATPIVAGNVAQLRE
     |||-||||+||||||||||||||||++||||||||||||||||||||||||
420  PDVTAPGTFILSARSSLAPDSSFWANYNSKYAYMGGTSMATPIVAGNVAQLRE

478  HFVKNRGVTPKPSLLKAALIAGAADVGLGFPNGNQGWGRVTLDKSLNVAFVNE
     ||+||||+|||||+|||||||||+|||||+|+|+||||||||||||||+|||
473  HFIKNRGITPKPSLIKAALIAGATDVGLGYPSGDQGWGRVTLDKSLNVAYVNE

531  TSPLSTSQKATYSFTAQAGKPLKISLVWSDAPGSTTASLTLVNDLDLVITAPN
     ++-|+|+|||||||-||||||||||||||+|||||||||-|||||||||||
526  ATALATGQKATYSFQAQAGKPLKISLVWTDAPGSTTASYTLVNDLDLVITAPN

584  GTKYVGNDFTAPYDNNWDGRNNVENVFINAPQSGTYTVEVQAYNVPVSPQTFS
     |-||||||+-|||||||||||||||||||||||||-+|||||||-+||-||
579  GQKYVGNDFSYPYDNNWDGRNNVENVFINAPQSGTYIIEVQAYNVPSGPQRFS

637  LAIVH
     |||||
632  LAIVH
```

NUCLEIC ACIDS ENCODING A POLYPEPTIDE HAVING PROTEASE ACTIVITY

BACKGROUND OF THE INVENTION

1. Field of the Invention

The present invention relates to isolated nucleic acid sequences encoding polypeptides having protease activity, in which the polypeptides are obtainable from an alkalophilic Bacillus species having enhanced stability towards bleaching agents of the peroxy type. The invention also relates to nucleic acid constructs, vectors, and host cells comprising the nucleic acid sequences as well as recombinant methods for producing the polypeptides.

2. Description of the Related Art

Detergents formulated with proteolytic enzymes are known to have improved properties for removing stains. For example, SAVINASE™ (Novo Nordisk A/S, Bagsvaerd, Denmark), a microbial protease obtained from *Bacillus lentus* has been introduced into many commercial brands of detergent.

WO 88/01293 discloses proteases obtained from an alkalophilic Bacillus species having enhanced stability towards bleaching agents of the peroxy type.

JP 1497182 discloses a DNA encoding an alkali protease Ya enzyme from Bacillus which is said to have good alkali and surfactant resistance and improves detergency.

Many detergents are alkaline in solution (e.g., around pH 10). There is a need for new proteolytic enzymes with high activity at high pH which are stable towards bleaching agents. Proteases of the type disclosed in WO 88/01293 possess these characteristics, and therefore, are highly desirable for use in detergent compositions. Heretofore, however, there has been no means of producing these enzymes recombinantly.

It is an object of the present invention to provide for recombinant production of these valuable enzymes.

SUMMARY OF THE INVENTION

The present invention relates to isolated nucleic acid sequences encoding a polypeptide having protease activity comprising an amino acid sequence which has at least 95% identity with the amino acid sequence set forth in SEQ ID NO:42; or an allelic form or a fragment thereof, wherein the fragment retains protease activity.

The present invention also relates to nucleic acid constructs, vectors, and host cells comprising the nucleic acid sequences as well as recombinant methods for producing the polypeptides.

BRIEF DESCRIPTION OF THE FIGURES

FIGS. 5A and 5B and 5C show the nucleic acid sequence and the deduced amino acid sequence of a Bacillus JP170 (NCIB 12513) protease gene (SEQ ID NOS:41 and 42, respectively).

FIGS. 6A and 6B show a comparison of the deduced amino acid sequence of a Bacillus JP170 (NCIB 12513) protease gene (SEQ ID NO:42) to the deduced amino acid sequences of the Ya protease (SEQ ID NO:43) and subtilisin (SEQ ID NO:44).

DETAILED DESCRIPTION OF THE INVENTION

Nucleic Acid Sequences

Figure 1:
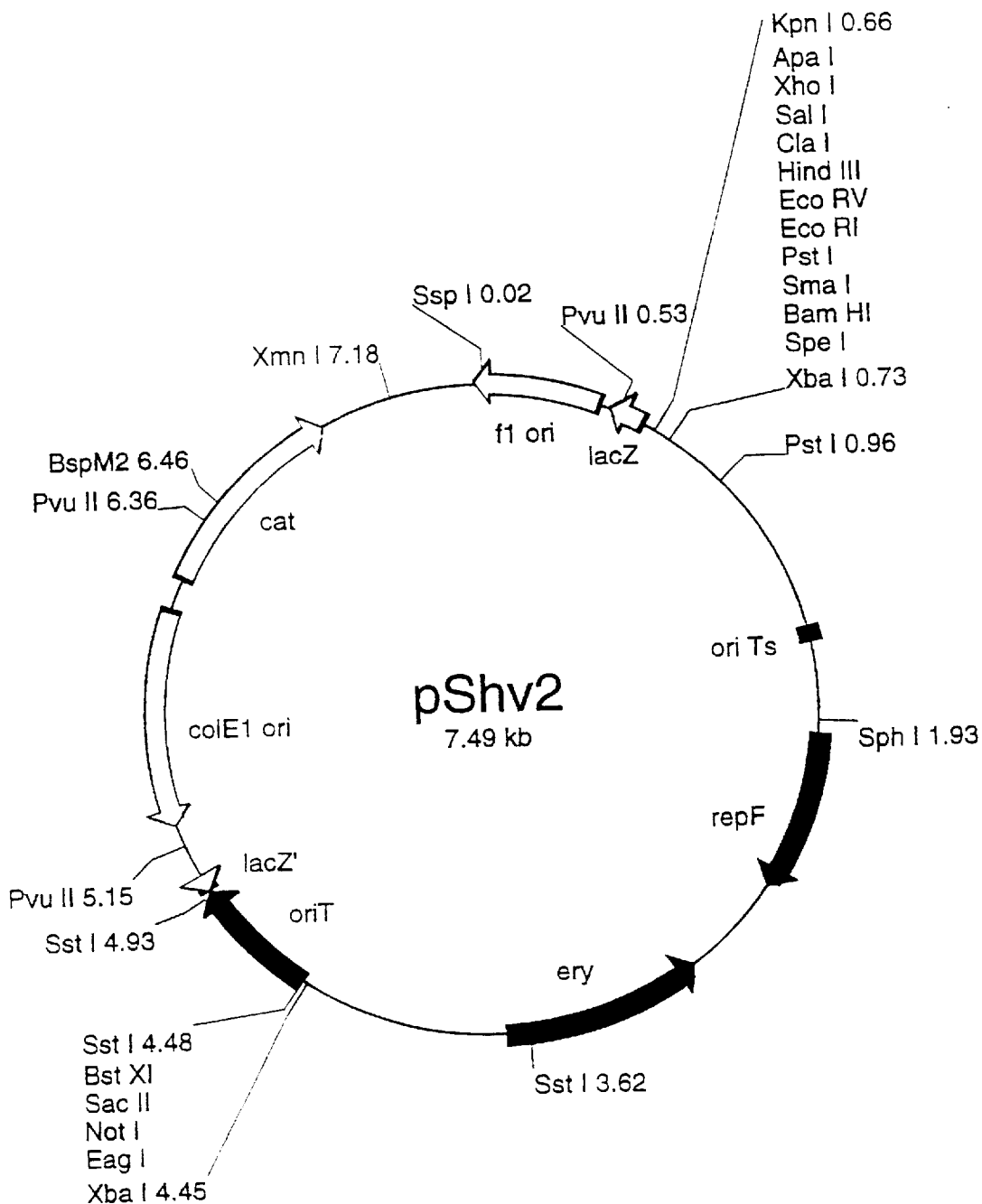
FIG. 1 shows a restriction map of pShv2.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined, for example, by agarose electrophoresis. An isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, or synthetic origin, or any combinations thereof.

The present invention relates to isolated nucleic acid sequences encoding polypeptides with protease activity comprising an amino acid sequence with a degree of identity to the amino acid sequence set forth in SEQ ID NO:42 of at least about 95% and preferably about 97%, which qualitatively retain the activity of the polypeptides (hereinafter "homologous polypeptides"), and allelic forms and fragments thereof, wherein the fragments retain protease activity. In a preferred embodiment, the homologous polypeptides comprise an amino acid sequence which differs by five amino acids, preferably by four amino acids, more preferably by three amino acids, even more preferably by two amino acids, and most preferably by one amino acid from the amino acid sequence set forth in SEQ ID NO:42. For purposes of the present invention, the degree of identity between two amino acid sequences or between nucleic acid sequences is determined by the Clustal method with an identity table, a gap penalty of 10, and a gap length penalty of 10 (Higgins, 1989, *CABIOS* 5: 151–153).

In a more preferred embodiment, the present invention relates to isolated nucleic acid sequences which encode polypeptides having protease activity comprising an amino acid sequence set forth in SEQ ID NO:42, and allelic forms and fragments thereof, wherein the fragments retain protease activity. In a specific embodiment, the nucleic acid sequence is set forth in SEQ ID NO:41, and allelic forms and fragments thereof, wherein the fragments retain protease activity. The nucleic acid sequences of the present invention also encompass nucleic acid sequences which encode a polypeptide comprising the amino acid sequence set forth in SEQ ID NO:42, but differ from SEQ ID NO:41 by virtue of the degeneracy of the genetic code. In a preferred embodiment, the nucleic acid sequence of the present invention is the nucleic acid sequence contained in plasmid p170BAN which is contained in *Bacillus subtilis* NRRL B-21680. The present invention also relates to subsequences of SEQ ID NO:41 which encode fragments of SEQ ID NO:42 which retain protease activity.

The amino acid sequences of the homologous polypeptides encoded by the nucleic acid sequences of the present invention may differ from the amino acid sequence set forth in SEQ ID NO:42 by an insertion or deletion of one or more amino acid residues and/or the substitution of one or more amino acid residues by different amino acid residues. Preferably, amino acid changes are of a minor nature, that is conservative amino acid substitutions which do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art and are described, e.g., by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In the present invention, the isolated nucleic acid sequences are capable of hybridizing under high, medium, or low stringency conditions with an oligonucleotide probe which hybridizes under the same conditions with the nucleic acid sequence set forth in SEQ ID NO:41 or its complementary strand (J. Sambrook, E. F. Fritsch, and T. Maniatis, 1989, *Molecular Cloning, A Laboratory Manual*, 2d edition, Cold Spring Harbor, N.Y.), and allelic forms and fragments thereof, wherein the fragments retain protease activity. Hybridization indicates that the analogous nucleic acid sequence hybridizes to the oligonucleotide probe corresponding to the polypeptide encoding part of the nucleic acid sequence shown in SEQ ID NO:41, under low to high stringency conditions (for example, prehybridization and hybridization at 42° C. in 5×SSPE, 0.3% SDS, 200 mg/ml sheared and denatured salmon sperm DNA, and either 50, 35 or 25% formamide for high, medium and low stringencies, respectively), following standard Southern blotting procedures. In a preferred embodiment, the nucleic acid sequences are capable of hybridizing under high stringency conditions with the nucleic acid sequence set forth in SEQ ID NO:41, its complementary strand, or a subsequence thereof.

SEQ ID NO:41 as well as SEQ ID NO:42, or subsequences thereof, may be used to design an oligonucleotide probe to isolate homologous genes encoding proteases from other strains of different genera or species according to methods well known in the art. Thus, a genomic or cDNA library prepared from such other organisms may be screened for DNA which hybridizes with such probes following standard Southern blotting procedures, in order to identify and isolate the corresponding gene therein. Such probes can be considerably shorter than the entire sequence, but should be at least 15, preferably at least 25, and more preferably at least 40 nucleotides in length. Longer probes, preferably no more than 1200 nucleotides in length, can also be used. Both DNA and RNA probes can be used. The probes are typically labeled for detecting the corresponding gene (for example, with $^{32}P$, $^{3}H$, biotin, or avidin).

Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify clones or DNA which are homologous with SEQ ID NO:41, the carrier material is used in a Southern blot in which the carrier material is finally washed three times for 30 minutes each using 2×SSC, 0.2% SDS at preferably not higher than 40° C., more preferably not higher than 45° C., more preferably not higher than 50° C., more preferably not higher than 55° C., even more preferably not higher than 60° C., especially not higher than 65° C. Molecules to which the oligonucleotide probe hybridizes under these conditions are detected using X-ray film.

The isolated nucleic acid sequences of the present invention which are capable of hybridizing with an oligonucleotide probe which hybridizes with the nucleic acid sequence set forth in SEQ ID NO:41, its complementary strand, or a subsequence thereof, may be obtained from microorganisms of any genus, for example, from a bacterial or fungal source, but preferably from a bacterial cell. For purposes of the present invention, the term "obtained from" (or endogenous to) as used herein in connection with a given source shall mean that the polypeptide is produced by the source or by a cell in which a gene from the source has been inserted. Preferred sources for homologous genes are strains of the genus Bacillus and species thereof available in public depositories. Furthermore, homologous genes may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Particularly preferred strains are bacterial strains, such as a Bacillus, Streptomyces, or Pseudomonas strain.

In a preferred embodiment, a nucleic acid sequence of the present invention is obtained from a strain of the genus Bacillus, as defined by Fergus G. Priest In Abraham L. Sonenshein, James A. Hoch, and Richard Losick, editors, *Bacillus subtilis* and Other Gram-Positive Bacteria, American Society For Microbiology, Washington, D.C., 1993, pages 3–16. Such strains include, but are not limited to, *Bacillus alkalophilus, Bacillus amyloliquefaciens, Bacillus brevis, Bacillus circulans, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis*. In a more preferred embodiment, the nucleic acid sequence is obtained from Bacillus strain NCIB 12513, e.g., the nucleic acid sequence set forth in SEQ ID NO:41.

Once a nucleic acid sequence has been detected with the probe(s) described above, the sequence may be isolated or cloned by utilizing techniques which are well known to those of ordinary skill in the art (see, e.g., Sambrook et al., 1989, supra). The known techniques used to isolate or clone a nucleic acid sequence include isolation from genomic DNA, preparation from cDNA, or a combination thereof. The cloning of the nucleic sequences of the present invention from such genomic DNA can be effected, e.g., by using the well known polymerase chain reaction (PCR). See, for example, Innis et al., 1990, *PCR Protocols: A Guide to Methods and Application*, Academic Press, New York. The nucleic acid sequence may be cloned from a strain of Bacillus producing the polypeptide, or another or related organism and thus, for example, may be an allelic or species variant of the polypeptide encoding region of the nucleic acid sequence.

Modification of the nucleic acid sequence encoding the polypeptide may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source. For example, it may be of interest to synthesize variants of the polypeptide where the variants differ in specific activity, thermostability, oxidative stability, pH optimum, or the like using, for example, site-directed mutagenesis. The analogous sequence may be constructed on the basis of the nucleic acid sequence presented as the polypeptide encoding region of SEQ ID NO:41, a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for protease activity to identify amino acid residues that are critical to the activity of the molecule. Sites of substrate-enzyme interaction can also be determined by analysis of crystal structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

Polypeptides encoded by the nucleic acid sequences of the present invention also include fused polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include, ligating the coding sequences encoding the polypeptides so that they are in frame and that expression of the fused polypeptide is under control of the same promoter(s) and terminator.

Nucleic Acid Constructs

The present invention also relates to nucleic acid constructs comprising a nucleic acid sequence of the present invention operably linked to one or more control sequences capable of directing the expression of the coding sequence in a suitable host cell under conditions compatible with the control sequences.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct may be synonymous with the term expression cassette when the nucleic acid construct contains all the control sequences required for expression of a coding sequence of the present invention. The term "coding sequence" as defined herein is a sequence which is transcribed into mRNA and translated into a polypeptide of the present invention when placed under the control of the appropriate control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

An isolated nucleic acid sequence of the present invention may be manipulated in a variety of ways to provide for expression of the polypeptide having protease activity. Manipulation of the nucleic acid sequence prior to its insertion into a vector may be desirable or necessary depending on the expression vector. The techniques for modifying nucleic acid sequences utilizing cloning methods are well known in the art.

The term "control sequences" is defined herein to include all components which are necessary or advantageous for expression of the coding sequence of the nucleic acid sequence. Each control sequence may be native or foreign to the nucleic acid sequence encoding the polypeptide. Such control sequences include, but are not limited to, a leader, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a Bacillus cell for expression of the nucleic acid sequence. The promoter sequence contains transcription control sequences which mediate the expression of the polypeptide. The promoter may be any nucleic acid sequence which shows transcriptional activity in the Bacillus cell of choice and may be obtained from genes encoding extracellular or intracellular polypeptides either homologous or heterologous to the Bacillus cell. Examples of suitable promoters for directing the transcription of the nucleic acid constructs of the present invention, especially in a Bacillus cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American,* 1980, 242: 74–94; and in Sambrook et al., 1989, supra.

The control sequence may also be a suitable transcription terminator sequence, a sequence recognized by a Bacillus cell to terminate transcription. The terminator sequence is operably linked to the 3' terminus of the nucleic acid sequence encoding the polypeptide. Any terminator which is functional in the Bacillus cell of choice may be used in the present invention.

The control sequence may also be a suitable leader sequence, a nontranslated region of a mRNA which is important for translation by the Bacillus cell. The leader sequence is operably linked to the 5' terminus of the nucleic acid sequence encoding the polypeptide. Any leader sequence which is functional in the Bacillus cell of choice may be used in the present invention.

The control sequence may also be a signal peptide coding region, which codes for an amino acid sequence linked to the amino terminus of the polypeptide which can direct the expressed polypeptide into the cell's secretory pathway. The signal peptide coding region may be native to the polypeptide of the invention or may be obtained from foreign sources. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide relative to the natural signal peptide coding region normally associated with the coding sequence. The signal peptide coding region may be obtained from an amylase or a protease gene from a Bacillus species. However, any signal peptide coding region capable of directing the expressed polypeptide into the secretory pathway of a Bacillus cell of choice may be used in the present invention.

An effective signal peptide coding region for Bacillus cells is the signal peptide coding region obtained from the maltogenic amylase gene from Bacillus NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* prsA gene. Further signal peptides are described by Simonen and Palva, 1993, *Microbiological Reviews* 57: 109–137.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i. e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid, two or more vectors or plasmids which together contain the total DNA to be introduced into the genome of the host cell, or a transposon.

The vectors of the present invention preferably contain one or more selectable markers which permit easy selection of transformed cells. A selectable marker is a gene the product of which provides for biocide resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, erythromycin, chloramphenicol or tetracycline resistance. Furthermore, selection may be accomplished by co-transformation, e.g., as described in WO 91/09129, where the selectable marker is on a separate vector.

The vectors of the present invention contain an element(s) that permits stable integration of the vector into the host cell genome or autonomous replication of the vector in the cell independent of the genome of the cell.

The vectors of the present invention may be integrated into the host cell genome when introduced into a host cell. For integration, the vector may rely on the nucleic acid sequence encoding the polypeptide or any other element of the vector for stable integration of the vector into the genome by homologous recombination. Alternatively, the vector may contain additional nucleic acid sequences for directing integration by homologous recombination into the genome of the host cell. The additional nucleic acid sequences enable the vector to be integrated into the host cell genome at a precise location in the chromosome. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in Bacillus. The origin of replication may be one having a mutation to make its function temperature-sensitive in the Bacillus cell (see, e.g., Ehrlich, 1978, *Proceedings of the National Academy of Sciences* USA 75: 1433).

More than one copy of a nucleic acid sequence encoding a polypeptide of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants. A convenient method for achieving amplification of genomic DNA sequences is described in WO 94/14968.

The procedures used to ligate the elements described above to construct the recombinant expression vectors of the present invention are well known to one skilled in the art (see, e.g., Sambrook et al., 1989, supra).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. Other examples of regulatory sequences are those which allow for gene amplification. In these cases, the nucleic acid sequence encoding the polypeptide would be operably linked with the regulatory sequence.

Host Cells

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome occurs by homologous or non-homologous recombination as described above.

The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis*; or a Streptomyces cell, e.g., *Streptomyces lividans* or *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell.

The transformation of a bacterial host cell may, for instance, be effected by protoplast transformation (see, e.g., Chang and Cohen, 1979, *Molecular General Genetics* 168: 111–115), by using competent cells (see, e.g., Young and Spizizin, 1961, *Journal of Bacteriology* 81: 823–829, or Dubnau and Davidoff-Abelson, 1971, *Journal of Molecular Biology* 56: 209–221), by electroporation (see, e.g., Shigekawa and Dower, 1988, *Biotechniques* 6: 742–751), or by conjugation (see, e.g., Koehler and Thorne, 1987, *Journal of Bacteriology* 169: 5771– 5278).

The host cell may also be a eukaryote, such as a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

Methods of Production

The present invention also relates to recombinant methods for producing a polypeptide of the present invention comprising (a) cultivating a host cell under conditions conducive to expression of the polypeptide; and (b) recovering the polypeptide.

In these methods, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see, e.g., M. V. Arbige et al., In Abraham L. Sonenshein, James A. Hoch, and Richard Losick, editors, *Bacillus subtilis* and Other Gram-Positive Bacteria, American Society For Microbiology, Washington, D.C., 1993, pages 871–895). Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it is recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. The production of protease activity can be determined by any method known in the art and include, e.g., measurement of fluorescence resulting from the hydrolysis of casein labeled with fluorescein isothiocyanate.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, New York, 1989).

Uses

The recombinant polypeptides encoded by the nucleic acid sequences of the present invention may be used in conventional applications of proteolytic enzymes, particularly at a high pH, e.g., in laundry and dishwashing detergents, institutional and industrial cleaning, and leather processing.

The recombinant polypeptides may also be used in numerous other applications including debittering or enhancing the degree of hydrolysis of protein hydrolysates, flavor development through hydrolysis of a protein, degradation of undesirable peptides, and enzymatic synthesis of peptides. The use of proteases in these and other applications are well established in the art.

The present invention is further described by the following examples which should not be construed as limiting the scope of the invention.

EXAMPLES

All primers and oligos were synthesized on an Applied Biosystems Model 394 Synthesizer (Applied Biosystems, Inc., Foster City, Calif.) according to the manufacturer's instructions.

Example 1

Construction of Bacillus subtilis Donor Strain BW154

Several genes (spoIIAC, aprE, nprE, amyE, and srfC) were deleted in the Bacillus subtilis A164 (ATCC 6051A) and 1630 (NCFB 736) host strains described herein. In order to accomplish this task, plasmids containing deleted versions of these genes were introduced into these strains using the pLS20-mediated conjugation system (Koehler and Thorne, 1987, supra). Briefly, this system is comprised of a Bacillus subtilis "donor" strain which contains a large plasmid designated pLS20. pLS20 encodes the functions necessary for mobilizing pLS20 into a "recipient" strain of Bacillus subtilis. In addition, it has been shown that plasmids such as pUB110 and pBC16 are also mobilized by this conjugation system (in the presence of pLS20). These plasmids contain a cis-acting region (oriT) and a gene (orf-beta) encoding a trans-acting function that acts at the oriT site and facilitates the mobilization of these plasmids into a recipient strain. Plasmids containing only oriT can also be mobilized if the donor strain contains both pLS20 and either pUB110 or pBC16 (in this case, orf-beta function is provided in trans).

The pLS20 plasmid or a derivative such as pXO503 (Koehler and Thorne, 1987, supra) must be present in order for a strain to be a proficient donor. In addition, it is also desirable to have a means of counter-selecting against the donor strain after the conjugation has been completed. A counter-selection scheme was developed that was very "clean" (no background) and easy to implement. This involved introducing a deletion in the dal gene of the donor strain (encodes the D-alanine racemase enzyme which is required for cell wall synthesis) and selecting against the donor strain by growing the cell mixture from a conjugation experiment on solid media devoid of D-alanine (this amino acid must be added exogenously to the media in order for a dal- strain of Bacillus subtilis to grow).

In order to delete the genes mentioned above, pE194 replicons (erythromycin resistance) (Gryczan et al., 1982, Journal of Bacteriology 152: 722–735) containing deleted versions of the genes and the oriT sequence had to be mobilized into the Bacillus subtilis A164 and A1630 strains. A suitable donor strain should have the following characteristics: 1) a deletion in the dal gene (for counter-selection) and 2) it must also contain pLS20 (pXO503 would be unsuitable in this case since the pE194 replicons must be maintained by erythromycin selection and pXO503 already confers resistance to this antibiotic) and either pUB110 or pBC16 to supply orf-beta function in trans. A description of how Bacillus subtilis BW154 was constructed as a donor strain follows.

(A) Introduction of a dal deletion in Bacillus subtilis to yield Bacillus subtilis BW96

First, a strain of Bacillus subtilis with a mutation in the bac-1 gene (this mutation abolishes the ability of the strain to synthesize the dipeptide antibiotic bacilysin) was chosen because it has been shown previously that wild-type Bacillus subtilis cells actually kill other species of Bacillus during the conjugation process and this killing potential is greatly reduced in cells which are bac-1-. Therefore, all donor strains have been constructed in a bac-1 background.

The first step in constructing a suitable donor strain was to delete a portion of the dal gene in the Bacillus subtilis strain 1A758 which is bac-1 (Bacillus Stock Center, Columbus, Ohio). A deleted version of the dal gene was constructed in vitro which could be exchanged for the wild-type dal gene on the bacterial chromosome. The 5' and 3' portions of the dal gene were PCR-amplified using primers 1 and 2 to amplify the 5' portion of the gene (nucleotides 19-419, the A of the ATG codon is +1) and primers 3 and 4 to amplify the 3' portion of the gene (nucleotides 618–1037).

Primer 1: 5'-GAGCTCACAGAGATACGTGGGC-3' (SEQ ID NO:1)

Primer 2: 5'-<u>GGATCC</u>ACACCAAGTCTGTTCAT-3' (SEQ ID NO:2) (BamHI site underlined)

Primer 3: 5'-<u>GGATCC</u>GCTGGACTCCGGCTG-3' (SEQ ID NO:3) (BamHI site underlined)

Primer 4: 5'-<u>AAGCTT</u>ATCTCATCCATGGAAA-3' (SEQ ID NO:4) (HindIII site underlined)

The amplification reactions (100 μl) contained the following components: 200 ng of Bacillus subtilis 168 chromosomal DNA, 0.5 μM of each primer, 200 μM each of dATP, dCTP, dGTP, and dTTP, 1×Taq polymerase buffer, and 1 U of Taq DNA polymerase. Bacillus subtilis 168 chromosomal DNA was obtained according to the procedure of Pitcher et al., 1989, Letters in Applied Microbiology 8: 151–156. The reactions were performed under the following conditions: 95° C. for 3 minutes, then 30 cycles each at 95° C. for 1 minute, 50° C. for 1 minute, and 72° C. for 1 minute, followed by 5 minutes at 72° C. Reactions products were analyzed by agarose gel electrophoresis. Both the 5' and 3' PCR products were cloned into the pCRII vector of the TA Cloning Kit (Invitrogen, San Diego, Calif.). according to the manufacturer's instructions. A pCRII clone was identified which contained the 5' half of the dal gene in an orientation such that the BamHI site introduced by the PCR primer was adjacent to the BamHI site of the pCRII polylinker (the other orientation would place the BamHI sites much farther apart). The pCRII clone containing the 3' half of the dal gene was then digested with BamHI and HindIII and the dal gene fragment was then cloned into the BamHI-HindIII site of the aforementioned pCRII clone containing the 5' half of the dal gene which generated a pCRII vector containing the dal gene with a ~200 bp deletion in the middle flanked by a NotI site at the 5' end (part of the pCRII polylinker) and a HindIII site at the 3' end of the gene.

In order to introduce this dal deletion into the bacterial chromosome, the deleted gene was cloned into the temperature-sensitive Bacillus subtilis replicon pE194 (Gryczan et al., 1982, supra). The deleted dal gene was then introduced into the chromosome in two steps: first by integrating the plasmid via homologous recombination into the chromosomal dal locus, followed by the subsequent removal of the plasmid (again via homologous recombination), leaving behind the deleted version of the dal gene on the bacterial chromosome. This was accomplished as follows: the deleted dal gene fragment (described above) was cloned into the NotI-HindIII site of the temperature sensitive plasmid pSK⁺/pE194 (essentially replacing the pSK⁺ vector sequences with the dalΔ fragment). Plasmid pSK⁺/pE194 was constructed as follows: both Bluescript SK⁺ (Stratagene, La Jolla, Calif.) and pE194 were digested with XbaI. The pSK⁺ vector was then treated with calf intestinal alkaline phosphatase and the two plasmids were ligated together. The ligation mix was used to transform the *E. coli* strain DH5α and transformants were selected on LB plates containing ampicillin (100 μg/ml) and X-gal. Plasmid was purified from several "white" colonies and a chimera consisting of both pE194 and pSK⁺ was identified by restriction enzyme digestion followed by gel electrophoresis. This plasmid was digested with HindIII and NotI. The fragment comprising the pE194 replicon was then gel-purified and ligated with gel-purified dalΔ gene fragment (HindIII-NotI). The ligation mix was used to transform the bac-1 strain *Bacillus subtilis* 1A758 (Bacillus Stock Center, Columbus, Ohio), and transformants were selected on Tryptone blood agar base (TBAB) plus erythromycin (5 μg/ml) plates and grown at the permissive temperature of 34° C. Plasmid DNA was purified from five erythromycin resistant transformants and analyzed by restriction enzyme digestion/gel electrophoresis. A plasmid was identified which corresponded to pE194 containing the dal-deleted fragment. The strain harboring this plasmid was subsequently used for the introduction of the dal deletion into the chromosome via homologous recombination.

In order to obtain the first cross-over (integration of the dal deletion plasmid into the dal gene on the chromosome), the transformed strain was streaked onto a TBAB plate containing D-alanine (0.1 mg/ml) and erythromycin (5 μg/ml) and grown overnight at the non-permissive temperature of 45° C. A large colony was restreaked under the same conditions yielding a homogeneous population of cells containing the temperature-sensitive plasmid integrated into the dal gene on the chromosome. At the non-permissive temperature, only cells which contain the plasmid in the chromosome were capable of growing on erythromycin since the plasmid was incapable of replicating. In order to obtain the second cross-over event (resulting in excision of the plasmid from the chromosome leaving behind the deleted version of the dal gene), a loopful of cells was transferred to 20 ml of Luria broth supplemented with D-alanine (0.1 mg/ml) and grown to late log phase without selection at the permissive temperature of 34° C. to permit function of the origin of replication and occurrence of the second cross-over event. Cells were transferred 4 times more (1/100 dilution each transfer) to allow the plasmid to excise from the chromosome and segregate out of the population. Finally, cells were plated for single colonies at 34° C. on TBAB plates supplemented with D-alanine (0.1 mg/ml) and replica-plated onto TBAB plates without D-alanine (0.1 mg/ml) and TBAB plates with D-alanine (0.1 mg/ml) and erythromycin (5 μg/ml) to score colonies which were dal- and erm$^s$. Two out of 50 colonies yielded this phenotype. The resulting strain was designated *Bacillus subtilis* BW96, a bac-1, dal- strain.

(B) Introduction of pLS20 and pBC16 into the bac-1, dal-deleted *Bacillus subtilis* strain to yield the conjugation proficient donor strain *Bacillus subtilis* BW154

A donor strain was chosen for introducing plasmids pLS20 and pBC16 into *Bacillus subtilis* BW96 wherein the donor strain should have the following characteristics: basically an erythromycin sensitive *Bacillus subtilis* strain (in order to provide a counter-selection against the donor strain) which contains both pLS20 and pBC16. A dal-deleted *Bacillus subtilis* strain containing pLS20 and pBC16 was chosen as a suitable donor strain which was constructed as follows: *Bacillus subtilis* DN1686 (U.S. Pat. No. 4,920,048) was transformed with pHV1248 (Petit et al., 1990, *Journal of Bacteriology* 172: 6736–6740) to make cells erythromycin resistant. The conjugative element pLS20 was transferred to the *Bacillus subtilis* DN1686 (pHV1248) strain along with pBC16 by conjugation with *Bacillus subtilis* (natto) 3335 UM8 (Koehler and Thorne, 1987, supra). The transconjugants were selected as tetracycline and erythromycin resistant colonies possessing a dal deletion. Colonies carrying pLS20 were scored by their ability to transfer pBC16 to other *Bacillus subtilis* strains by conjugation. Finally the conjugative strain was cured of pHV1248 by raising the temperature to 50° C. yielding the donor strain: *Bacillus subtilis* DN1686 containing pLS20 and pBC16.

In order to introduce these plasmids into *Bacillus subtilis* BW96, a suitable counter-selection scheme had to be implemented, and therefore, *Bacillus subtilis* BW96 was transformed with a temperature-sensitive plasmid pSK+/pE194 conferring erythromycin resistance which could be subsequently removed by growth at a non-permissive temperature. The pLS20 and pBC16 plasmids were mobilized from *Bacillus subtilis* DN1686 containing pLS20 and pBC16 into *Bacillus subtilis* BW96 (harboring pSK⁺/pE194) according to the following procedure. A loopful of each cell type was mixed together on a TBAB plate supplemented with D-alanine (50 μg/ml) and incubated at 33° C. for 5 hours. The cells were scraped from the plate and transferred to 1 ml of LB medium. The cells were spread at various dilutions onto TBAB plates supplemented with tetracycline (10 μg/ml), erythromycin (5 μg/ml), and D-alanine (50 μg/ml) and grown at 34° C. to select for recipient cells which acquire pBC16 and in many cases pLS20 as well. To test whether pLS20 was also present in any of the transconjugants, ten colonies were tested for their ability to transfer pBC16 into *Bacillus subtilis* PL1801. *Bacillus subtilis* PL1801 is *Bacillus subtilis* 168 (Bacillus Stock Center, Columbus, Ohio) with deletions of the genes apr and npr). However, *Bacillus subtilis* 168 may also be used. Donors capable of mobilizing pBC16 must contain pLS20 as well. Once a conjugation proficient strain was identified (*Bacillus subtilis* bac-1, dal- containing pLS20 plus pBC16 plus pSK⁺/pE194), the pSK⁺/pE194 plasmid was cured from the strain by propagating the cells in LB medium supplemented with tetracycline (5 μg/ml) and D-alanine (50 μg/ml) overnight at 45° C., plating for single colonies at 33° C. on TBAB plates supplemented with D-alanine (50 μg/ml), and identifying erythromycin sensitive colonies. This procedure yielded *Bacillus subtilis* BW154 which is *Bacillus subtilis* bac-1, dal- containing pLS20 and pBC16.

A summary of the Bacillus strains and plasmids is presented in Table I.

TABLE I

Bacterial strains and plasmids

*Bacillus subtilis* strains:

| | |
|---|---|
| *B. subtilis* (natto) | pLS20 |
| DN1686 | dal- |
| DN1280 | dal- |

TABLE I-continued

Bacterial strains and plasmids

Bacillus subtilis strains:

| | |
|---|---|
| MT101 | DN1280 (pXO503) |
| 1A758 | 168 bac-1 (Bacillus Stock Center, Columbus, Ohio) |
| BW96 | 1A758 dalΔ |
| BW97 | 1A758 dalΔ::cat (pXO503) |
| BW99 | 1A758 dalΔ (pPL2541-tet) |
| BW100 | 1A758 dalΔ (pXO503), (pPL2541-tet) |
| PL1801 | aprΔ,nprΔ |

Plasmids:

| | |
|---|---|
| pBC16 | Mob$^+$, Tc$^r$ |
| pE194 | temperature sensitive |
| pLS20 | Tra$^+$ |
| pXO503 | Tra$^+$, MLS$^r$ (=pLS20::Tn917) |
| pPL2541-tet | Mob$^+$, Tc$^r$(pE194 ts ori) |
| pCAsub2 | Mob$^+$, Cm$^r$, Ap$^r$, (pE194 ts ori) |
| pSK$^+$/pE194 | Em$^r$, Ap$^r$, temperature-sensitive |
| pShv2 | Tra$^+$, Em$^r$, Cm$^r$, temperature-sensitive |
| pHV1248 | Em$^r$, temperature-sensitive |

Tra$^+$ implies that the plasmid confers upon any *Bacillus subtilis* strain bearing it the ability to conjugate, that is, the plasmid encodes all of the functions for mobilizing a conjugatable plasmid from the donor to a recipient cell.

Mob$^+$ implies that a plasmid is capable of being mobilized via conjugation by a strain which contains a Tra$^+$ plasmid (pLS20 or pXO503). The plasmid must contain a cis-acting sequence and a gene encoding a trans-acting protein (oriT and orf-beta, respectively, in the case of pBC16) or just an oriT sequence (in the case of pPL254-tet, here a plasmid supplying orf-beta function in trans such as pBC16 must also be present in the cell as well).

Example 2

Deletion of the spoIIAC Gene of *Bacillus subtilis* A164 (ATCC 6051A)

A deleted version of the spoIIAC gene which encodes sigma F permitting cells to proceed through stage II of sporulation was created by splicing by overlap extension (SOE) technique (Horton et al., 1989, *Gene* 77: 61–68). *Bacillus subtilis* A164 (ATCC 6051A) chromosomal DNA was obtained by the method of Pitcher et al., 1989, supra. Primers 5 and 6 shown below were synthesized for PCR amplification of a region from *Bacillus subtilis* A164 chromosomal DNA extending from 205 nucleotides upstream of the ATG start codon of the spoIIAC gene to 209 nucleotides downstream of the ATG start. The underlined nucleotides of the upstream primer were added to create a HindIII site. The underlined nucleotides of the downstream primer were complementary to bases 507 to 524 downstream of the ATG translational start codon. Primers 7 and 8 were synthesized to PCR-amplify a region extending from 507 to 884 nucleotides downstream of the ATG translational start codon. The underlined region of primer 7 was exactly complementary to the 3' half of primer 6 used to amplify the upstream fragment.

Primer 5: 5'-<u>AAGCTT</u>AGGCATTACAGATC-3' (SEQ ID NO:5)

Primer 6: 5'-<u>CGGATCTCCGTCATTTT</u>CCAGCCCGATGCAGCC-3' (SEQ ID NO:6)

Primer 7: 5'-<u>GGCTGCATCGGGCTGG</u>AAAATGACGGAGAT- CCG-3' (SEQ ID NO:7)

Primer8: 5'-GATCACATCTTCGGTGG-3' (SEQ ID NO:8)

The two sets of primers were used to amplify the upstream and downstream spoIIAC fragments in separate PCR amplifications. The amplification reactions (25 μl) contained the following components: 200 ng of *Bacillus subtilis* A 164 chromosomal DNA, 0.5 μM of each primer, 200 μM each of dATP, dCTP, dGTP, and dTTP, 1×Taq polymerase buffer, and 0.625 U of Taq DNA polymerase. *Bacillus subtilis* A164 chromosomal DNA was obtained according to the procedure of Pitcher et al., 1989, supra. The reactions were performed under the following conditions: 96° C. for 3 minutes, then 30 cycles each at 96° C. for 1 minute, 50° C. for 1 minute, and 72° C. for 1 minute, followed by 3 minutes at 72° C. to insure addition of a terminal adenine residue to the amplified fragments (Invitrogen, San Diego, Calif.). Amplification of the expected products was verified by electrophoresis through a 1.5% agarose gel.

A new PCR mixture containing 2.5 μl of each amplification reaction above was then performed under the same conditions but containing only primers 5 and 8, producing a "spliced" fragment of 1089 nucleotides, representing the spoIIAC gene lacking 298 internal nucleotides. This fragment was cloned into the pCRII vector using the Invitrogen TA Cloning Kit according to the manufacturer's instructions, excised as a HindIII-EcoRI fragment, and then cloned into HindIII/EcoRI-digested pShv2. pShv2 (FIG. 1) is a shuttle vector constructed by ligating XbaI-cut pBCSK$^+$ (Stratagene, La Jolla, Calif.) containing oriT of pUB110 with XbaI-cut pE194, followed by ligation of oriT from pUB110 as a PCR-amplified fragment containing SstI compatible ends. The oriT fragment permits mobilization of the plasmid into *Bacillus subtilis* A164 by pLS20-mediated conjugation (Battisti et al., 1985, *Journal of Bacteriology* 162: 543–550). pShv2-ΔspoIIAC was transformed into donor strain *Bacillus subtilis* BW154 (Example 1). *Bacillus subtilis* BW154 (pShv2-ΔspoIIAC) was used as a donor strain to introduce the shuttle vector containing the deleted gene into *Bacillus subtilis* A164.

Exchange of the deleted gene with the intact chromosomal gene was effected by conjugation of *Bacillus subtilis* BW154 transformed with pShv2-ΔspoIIAC with *Bacillus subtilis* A164, selection of erythromycin-resistant transconjugants, and growth at 45° C. At this temperature, the pE194 replicon was inactive, and cells were only able to maintain erythromycin resistance by Campbell integration of the plasmid containing the deleted gene at the spoIIAC locus. A second recombination event, resulting in loopout of vector DNA and replacement of the intact spoIIAC gene with the deleted gene, was effected by growth of the strain for two rounds in LB medium without antibiotic selection at 34° C., a temperature permissive for function of the pE194 replicon. Colonies in which gene replacement had occurred were selected according to the following criteria: 1) absence of erythromycin (erm) resistance encoded by the shuttle vector pShv2, 2) decreased opacity on sporulation medium, indicating failure to sporulate, and 3) PCR amplification with primers 5 and 8 to obtain a fragment of 791 nucleotides instead of 1089 nucleotides representing the undeleted version of the gene.

Example 3

Deletion of the nprE Gene of *Bacillus subtilis* A164 -ΔspoIIAC

An upstream portion of the neutral protease (nprE) gene (nucleotides 40–610 downstream of the GTG start codon) was PCR-amplified from *Bacillus subtilis* A164 ΔspoIIAC chromosomal DNA prepared in the manner described in Example 2 using primers 9 and 10 shown below. A downstream portion of the nprE gene (nucleotides 1040–1560) was PCR amplified using primers 11 and 12 shown below. Primers 10 and 11 were designed such that there would be a 15 base pair overlap between the two fragments (denoted by underlining). The amplification reactions (25 μl) contained the same components and were performed under the same conditions specified in Example 2.

Primer 9: 5'-CGTTTATGAGTTTATCAATC-3' (SEQ ID NO:9)

Primer 10: 5'-<u>AGACTTCCCAGTTTG</u>CAGGT-3' (SEQ ID NO:10)

Primer 11: 5'-<u>CAAACTGGGAAGTCT</u>CGACGGTTC-ATTCTTCTCTC-3' (SEQ ID NO:11)

Primer 12: 5'-TCCAACAGCATTCCAGGCTG-3' (SEQ ID NO:12)

The amplified upstream and downstream fragments were gel purified with the Qiaex II Kit according to the manufacturer's instructions (Qiagen, Chatsworth, Calif.). A new PCR mixture (100 μl) containing approximately 20 ng of each purified fragment was performed. The SOE reaction was performed under the following conditions: cycles 1–3 in the absence of primers to generate a "spliced" fragment, and cycles 4–30 in the presence of primers 9 and 12 under the conditions specified in Example 2. The amplified SOE fragment was cloned into the pCRII vector and verified by restriction analysis. The fragment was then cloned into pShv2 as a BamHI-XhoI fragment. This plasmid, pShv2-ΔnprE, was transformed into *Bacillus subtilis* BW154 to generate a suitable donor strain for conjugation. The plasmid was then mobilized into *Bacillus subtilis* A164 ΔspoIIAC. The ΔnprE gene was introduced into the chromosome of *Bacillus subtilis* A164 ΔspoIIAC by temperature shift as described in Example 2. An nprE- phenotype was scored by patching erm$^s$ colonies onto TBAB agar plates supplemented with 1% non-fat dry milk and incubating overnight at 37° C. (An nprE- strain had a noticeably reduced clearing zone.) The 430 base pair deletion was verified by PCR analysis on chromosomal DNA using primers 9 and 12.

Example 4

Deletion of the aprE Gene of *Bacillus subtilis* A164 ΔspoIIAC ΔnprE

SOE was used to create a deleted version of the *Bacillus subtilis* aprE gene which encodes an alkaline subtilisin protease. An upstream portion of aprE was PCR amplified using primers 13 and 14 shown below from *Bacillus subtilis* A164 chromosomal DNA prepared as described in Example 2 to create a fragment extending from 189 nucleotides upstream of the translational start codon to 328 nucleotides downstream of the start. The underlined nucleotides of primer 13 were included to add an EcoRI site. The underlined nucleotides of primer 14 were added to provide complementarity to the downstream PCR fragment and to add a SalI site. A downstream portion of the aprE gene was PCR-amplified using primers 15 and 16 to create a fragment extending from 789 nucleotides to 1306 nucleotides downstream of the aprE translational start codon. Underlined regions of primers 14 and 15 were added to provide complementarity between the upstream and downstream fragments. The underlined nucleotides of primer 16 were included to add a HindIII site. The amplification reactions (25 μl) contained the same components and were conducted under the same conditions as described in Example 2.

Primer 13: 5'-GC<u>GAATTC</u>TACCTAGAGATAAAATC-3' (SEQ ID NO:13)

Primer 14: 5'-<u>GTTTACCGCACCTACGTCGAC</u>CCTGTGTAGCCTTGA-3' (SEQ ID NO:14)

Primer 15: 5'-<u>TCAAGGCTACACAGGGTCGAC</u>GTAGGTGCGGTAAAC-3' (SEQ ID NO:15)

Primer 16: 5'-GC<u>AAGCTT</u>GACAGAGAGAACAGAAGCCAG-3' (SEQ ID NO:16)

The amplified upstream and downstream fragments were purified using the Qiaquick PCR Purification Kit according to the manufacturer's instructions (Qiagen, Chatsworth, Calif.). The two purified fragments were then spliced together using primers 13 and 16. The amplification reaction (50 μl) contained the same components as above except the chromosomal DNA was replaced with 2 μl each of the upstream and downstream PCR products. The reactions were incubated for 1 cycle at 96° C. for 3 minutes (without the dNTPs and Taq polymerase), and then for 30 cycles each at 96° C. for 1 minute and 72° C. for 1 minute. This resulted in a deleted version of aprE lacking 460 nucleotides from the coding region. The reaction product was isolated by agarose electrophoresis, cloned into pCRII, excised as an EcoRI-HindIII fragment, and then cloned into EcoRI/HindIII-digested pShv2 to yield pShv2-ΔaprE. This plasmid was introduced into the donor strain described above for conjugal transfer into *Bacillus subtilis* A164 ΔspoIIAC ΔnprE.

Replacement of aprE with the deleted gene was effected as described above for spoIIAC and nprE. Colonies in which aprE had been deleted were selected by erythromycin sensitivity and reduced clearing zones on agar plates with an overlay containing 1% non-fat dry milk. Deletion of aprE was confirmed by PCR.

*Bacillus subtilis* A164 ΔspoIIAC ΔnprE ΔaprE is herein designated *Bacillus subtilis* A164 Δ3.

Example 5

Deletion of the amyE Gene of *Bacillus subtilis* A164 ΔspoIIAC ΔnprE ΔaprE

SOE was used to create a deleted version of the amyE gene which encodes *Bacillus subtilis* alpha-amylase. An upstream portion of amyE was PCR-amplified from *Bacillus subtilis* A164 chromosomal DNA using primers 17 and 18 shown below. This created a fragment extending from 421 nucleotides upstream of the amyE translational start codon to nucleotide 77 of the amyE coding sequence, adding a SalI site at the upstream end and SfiI and NotI sites at the downstream end. A downstream portion of amyE was PCR-amplified using primers 19 and 20 shown below. This created a fragment extending from nucleotide 445 to nucleotide 953 of the amyE coding sequence, and added SfiI and NotI sites at the upstream end and a HindIII site at the downstream end. Restriction sites are denoted by underlining. The amplification reactions (25 μl) contained the same components and were conducted under the same conditions as described in Example 2.

The two fragments were then spliced together by PCR using primers 17 and 20. The amplification reaction (25 μl) contained the same components as above except the chromosomal DNA was replaced with 2 μl each of the upstream and downstream PCR products. The reactions were incubated for 1 cycle at 96° C. for 3 minutes (without the dNTPs and Taq polymerase), and then at 96° C. for 1 minute and 72° C. for 1 minute for 30 cycles. This reaction fused the two fragments by overlap at the region of complementarity between the two (the SfiI and NotI sites) and resulted in a fragment of amyE lacking 367 nucleotides from the coding region and having an SfiI site and a NotI site incorporated between the two portions of amyE. The reaction product was isolated by electrophoresis using a 1% agarose gel according to standard methods. This fragment was cloned into pCRII according to the manufacturer's instructions to yield pCRII-ΔamyE.

Primer 17: 5'-CGTCGACGCCTTTGCGGTAGTGGTGCTT-3' (SEQ ID NO:17) (SalI site underlined)

Primer 18: 5'-CGCGGCCGCAGGCCCTTAAGGCCAGAACCAAATGAAA-3' (SEQ ID NO:18) (NotI and SfiI sites underlined)

Primer 19: 5'-TGGCCTAAGGGCCTGCGGCCGATTTCCAATG-3' (SEQ ID NO:19) (SfiI and NotI sites underlined)

Primer 20: 5'-GAAGCTTCTTCATCATCATTGGCATACG-3' (SEQ ID NO:20) (HindIII site underlined)

pShv2.1 was created by digesting pShv2 with NotI, filling in the cohesive ends with Klenow fragment and dNTPs, and religating the plasmid. This procedure destroyed the NotI recognition site of pShv2. The deleted amyE fragment was excised from pCRII-ΔamyE as a SalI-HindIII fragment and cloned into SalI/HindIII-digested pShv2. 1 to yield pShv2.1-ΔamyE. This plasmid was introduced into *Bacillus subtilis* BW154 for conjugal transfer into *Bacillus subtilis* A164 ΔspoIIAC ΔnprE ΔaprE.

Replacement of amyE with the deleted gene was effected as described above for spoIIAC, nprE, and aprE. Colonies in which gene replacement had occurred were selected by erythromycin sensitivity and the inability to produce a zone of clearing on starch azure overlay plates. Deletion of amyE was confirmed by PCR amplification of the deleted gene from chromosomal DNA using primers 17 and 20.

Example 6

Deletion of the srfC Gene of *Bacillus subtilis* A164 ΔspoIIAC Δnpr Δapr ΔamyE to Produce *Bacillus subtilis* A164 ΔspoIIAC ΔnprE ΔaprE ΔamyE ΔsrfC Primers 21–24 shown below were synthesized for the creation of a deletion in srfC of the surfactin operon. Primer 21 overlaps an existing HindIII site (underlined) in the srfC gene, and in conjunction with primer 22 permits PCR amplification of a region extending from 410 nucleotides to 848 nucleotides downstream of the translational start of srfC. The underlined portion of primer 22 was complementary to nucleotides 1709–1725 downstream of the ATG start codon. Primers 23 and 24 permit PCR amplification of a region of 1709 to 2212 nucleotides downstream of the translational start of srfC. The underlined portion of primer 23 was complementary to nucleotides 835–848 downstream of the ATG codon. The amplification reactions (25 μl) contained the same components and were performed under the same conditions as described in Example 2.

Primer 21: 5'-AAGCTTTGAATGGGTGTGG-3' (SEQ ID NO:21)

Primer 22: 5'-CCGCTTGTTCTTTCATCCCCTGAAACAACTGTACCG-3' (SEQ ID NO:22)

Primer 23: 5'-CAGTTGTTTCAGGGGATGAAAGAACAAGCGGCTG-3' (SEQ ID NO:23)

Primer 24: 5'-CTGACATGAGGCACTGAC-3' (SEQ ID NO:24)

Primers and other contaminants were removed from the PCR products with a Qiagen PCR spin column (Qiagen, Chatsworth, Calif.). The complementarity between the two PCR-generated fragments permitted splicing by SOE. The PCR products (2 μl or approximately 50 ng each) were spliced together under the same PCR conditions as described above with the "outside primers", primers 21 and 24, except that the first 3 cycles were performed before addition of the primers to extend the overlapping regions. The SOE reaction resulted in a 955 nucleotide fragment that lacked an internal 859 nucleotides of the srfC gene. The deleted portion represents the region of srfC responsible for addition of the seventh amino acid leucine to the surfactin molecule, and furthermore results in a frameshift mutation which results in termination of the peptide prior to the thioesterase active site-like region, presumed to be involved in surfactin release from the SrfC protein (Cosmina et al., 1993, supra).

Replacement of srfC with the deleted gene was effected as described above for spoIIAC, nprE, and aprE, and amyE. Colonies in which gene replacement had occurred were selected by erythromycin sensitivity, the inability to produce a zone of clearing on blood agar plates (Grossman et al, 1993, *Journal of Bacteriology* 175: 6203–6211), and lack of foaming upon cultivation for 4 days at 37° C. and 250 rpm in 250 ml shake flasks containing 50 ml of PS-1 medium composed of 10% sucrose, 4% soybean flour, 0.42% anhydrous disodium phosphate, and 0.5% calcium carbonate supplemented with 5 μg of chloramphenicol per ml. Deletion of srfC was confirmed by PCR amplification of the deleted gene from chromosomal DNA using primers 21 and 24.

*Bacillus subtilis* A164 ΔspoIIAC ΔnprE ΔaprE ΔamyE ΔsrfC is herein designated *Bacillus subtilis* A 164 Δ5.

Example 7

Construction of *Bacillus subtilis* A1630 ΔspoIIAC ΔnprE ΔaprE ΔamyE ΔsrfC

*Bacillus subtilis* A1630 ΔspoIIAC ΔnprE ΔaprE ΔamyE ΔsrfC was constructed from *Bacillus subtilis* A1630 (NCFB 736, formerly NCDO 736) according to the same procedures described in Examples 1–6 for *Bacillus subtilis* A164 ΔspoIIAC ΔnprE ΔaprE ΔamyE ΔsrfC (*Bacillus subtilis* A164 Δ5), using the deletion plasmids constructed for the Bacillus subtilis A164 deletions.

*Bacillus subtilis* A1630 ΔspoIIAC Δnpr Δapr ΔamyE ΔsrfC is herein designated *Bacillus subtilis* A1630 Δ5.

Example 8

Preparation of Chromosomal DNA of Bacillus JP170

Bacillus JP170 (NCIB 12513) was grown overnight at 37° C. in 50 ml of Luria-Bertani (LB) broth containing 0.1M NaHCO$_3$ pH 8. Genomic DNA was prepared according to the method of Pitcher et al., 1989, supra.

Example 9

Preparation of Probes of the Bacillus JP170 Protease Gene

Based on the N-terminal and internal amino acid sequences of the Bacillus JP170 protease (JP 4197182) shown below, primers were synthesized to clone the Bacillus JP170 protease gene: N-terminus: NDVARGIVKADVAQNNFGLYGQGQIVADTGLDTGRNDS (SEQ ID NO:25)

Internal peptide: GAADVGLGFPNGNQGWGRVTLDK (SEQ ID NO:26)

The primers designated 170–291, 1701, and 1702B shown below (where I=inosine) were used in the amplification reactions described below.

170–291: 5'-CCCCAICCITGITTICCITTIGGIAAICC-3' (SEQ ID NO:27)

1701: 5'-GGIATIGTIAAIGCIGAIGTIGCICAIAA-IAAITTIGG-3' (SEQ ID NO:28)

1702B: 5'-TAIGGICAIGGICAIATIGTIGCIGTIGC-IGAIACIGG-3' (SEQ ID NO:29)

Amplification reactions were prepared with 50 pmol of either primers 1701 and 170–291 or 1702B and 170–291, 7 µg of Bacillus JP170 chromosomal DNA as template, 1×PCR buffer (Perkin-Elmer, Foster City, Calif.), 100 µM each of dATP, dCTP, dGTP, and dTTP, and 0.5 U of AmpliTaq Gold (Perkin-Elmer, Foster City, Calif.). Reactions were incubated in a Stratagene Robocycler 40 (Stratagene, La Jolla, Calif.) programmed for 1 cycle at 96° C. for 3 minutes and 30 cycles each at 40° C. for 1 minute, 40° C. for 1 minute, and 72° C. for 1 minute.

Amplification with primers 170–291 and 1701 resulted in a 905 bp product designated 1/291, and with primers 1702B and 170–291 an 863 bp product designated 2B/291. Both PCR products were individually cloned into the Invitrogen TA Cloning Kit vector pCR2.1 (Invitrogen, San Diego, Calif.) according to the manufacturer's instructions. Sequencing with an Applied Biosystems Model 377 Sequencer (Applied Biosystems, Foster City, Calif.) showed that these PCR products had 90% identity to the amino acid sequence of the Ya protease disclosed in JP 4197182 based on alignment of the deduced amino acid sequences in the GeneAssist 1.1b4 database (Applied Biosystems, Foster City, Calif.). The amino acid sequence of the PCR product also had a 35% identity to the amino acid sequence of the Bacillus serine protease subtilisin.

Primers 170–291, 1701, and 1702B were then used to PCR-amplify DIG-labeled probes of 1/291 and 2B/291 using the Genius System PCR DIG Probe Synthesis Kit (Boehringer Mannheim Corporation, Indianapolis, Ind.) according to the manufacturer's under the same PCR conditions as described above.

Example 10

Screening of Chromosomal Libraries

Figure 2:
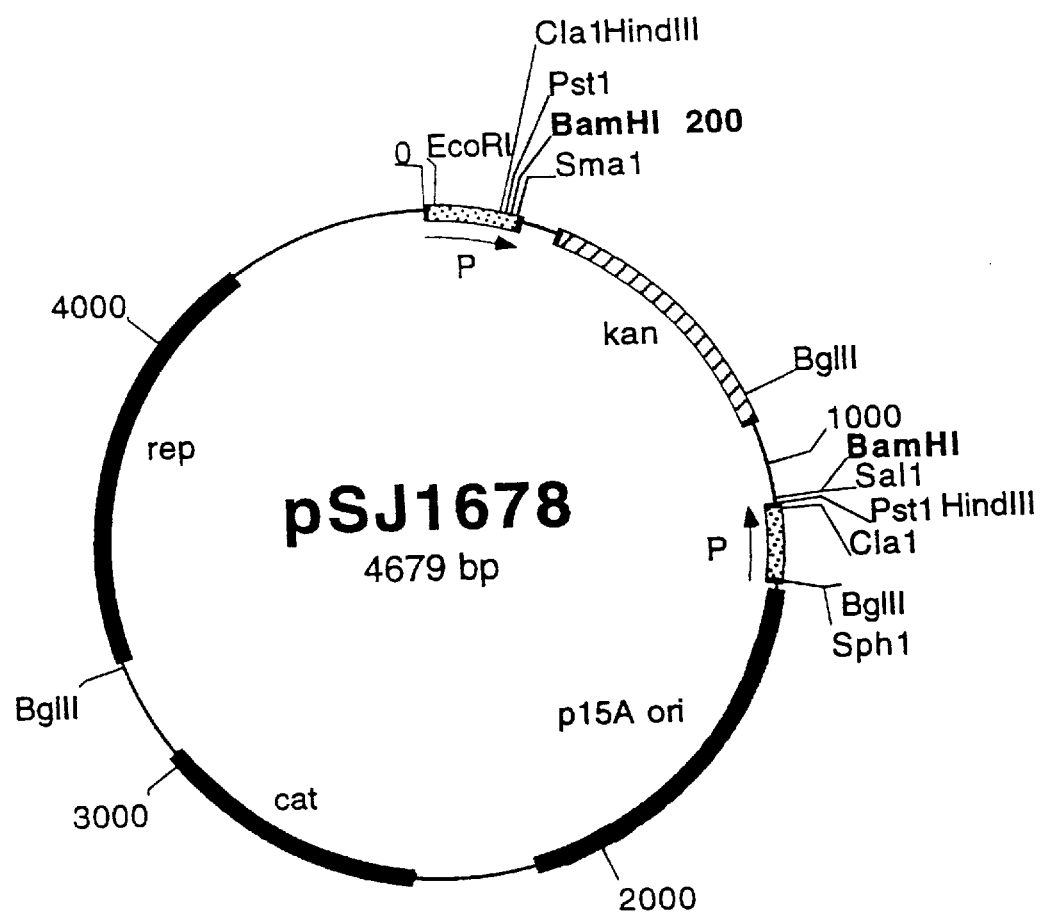
FIG. 2 shows a restriction map of pSJ1678.

Probe 2B/291 described in Example 9 was used to screen a chromosomal library of Bacillus JP170. The library was constructed by ligating Sau3A partially-digested (4–8 kb) Bacillus JP170 chromosomal DNA into the BamHI sites of the vector pSJ1678 (FIG. 2). *Escherichia coli* DH5α (Gibco BRL, Gaithersburg, Md.) was transformed with the chromosomal library and screened by colony lifts using the DIG-labeled probe 2B/291 following the Genius System instructions. After screening approximately 4600 colonies, 1 colony hybridized to the probe and was designated Clone 1. Plasmid DNA from Clone 1 was prepared using a QIAprep 8 Plasmid Kit (Qiagen, Chatsworth, Calif.). Restriction digests of plasmid DNA indicated that Clone 1 contained an insert of approximately 13 kb.

DNA from Clone 1 and Bacillus JP170 chromosomal DNA were analyzed by Southern hybridization using 2B/291 as a probe. Specifically, 7 µg of Bacillus JP170 chromosomal DNA and 16 ng of Clone 1 plasmid DNA was digested with EcoRI and HindIII and the digests were electrophoresed on a 1% agarose gel. The DNA was capillary transferred onto a Nytran Plus membrane (Schleicher and Schuell, Keene, N.H.) following the manufacturer's instructions. The membrane was then probed following the Genius System instructions.

The Southern hybridization results demonstrated that the 2B/291 probe hybridized with 2 bands of 1800 and 1400 bp from the EcoRI digested chromosomal DNA and with 2 bands of approximately 2000 and 1800 bp from the EcoRI digested Clone 1 DNA. The 2B/291 probe also hybridized with 2 bands of 2000 and 1800 bp from the HindIII digested chromosomal DNA and with 1 band of approximately 2000 bp from the HindIII digested Clone 1 DNA. These results indicated that Clone 1 did not contain the entire gene since only the single 2000 bp band hybridized with the 2B/291 probe. Sequencing of the HindIII fragment from Clone 1 suggested it contained a partial open reading frame which contained 1200 bp of the 5' end of the protease gene, based on homology to the protease disclosed in JP 4197182.

Since the Southern hybridization results indicated that the 3' end was located on an 1800 bp HindIII fragment, a new library was constructed. Bacillus JP170 chromosomal DNA was digested with HindIII and the digest electrophoresed on a 1% agarose gel. Fragments ranging in size from 1500 bp to 2200 bp were excised and purified using a QIAquick Gel Extraction Kit (Qiagen, Chatsworth, Calif.). These fragments were then ligated into the HindIII site of pUC118. *E. coli* DH5α (Gibco BRL, Gaithersburg, Md.) was transformed with the ligation following the manufacturer's instructions and transformants were screened using the 2B/291 probe as described above. After screening 3200 transformants, 5 positive transformants were identified. Plasmid DNA from each of the 5 transformants was prepared using a QIAprep 8 Plasmid Kit according to the manufacturer's instructions and digested with HindIII. The resulting restriction fragments were compared to Clone 1 plasmid DNA restriction fragments by gel electrophoresis. All 5 clones contained fragments identical in size to the previously cloned 5' end of the Bacillus JP170 protease gene.

Example 11

Isolation of the 3' end of the Bacillus JP170 Protease Gene by Inverse PCR

Inverse PCR was used to isolate the 3' end of the Bacillus JP170 protease gene by amplifying the region downstream of the chromosomal clone isolated in the library screen (Clone 1) described in Example 10. Southern hybridization of chromosomal DNA showed that the 3' end of the gene should be contained on an 1800 bp EcoRI fragment (Example 10). Size-selected chromosomal DNA was prepared by digestion of the Bacillus JP170 chromosomal DNA with EcoRI followed by electrophoresis on a 1% agarose gel. Fragments ranging from approximately 1600 bp to 2000 bp were isolated using a QIAquick Gel Extraction Kit and eluted in 30 µl of TE. The EcoRI fragments were self-ligated in a 10 µl ligation reaction containing the following components: 1 µl of size-selected DNA, 1×ligation buffer (Boerhinger Mannheim, Indianapolis, Ind.), and 1 unit of T4 DNA Ligase (Boehringer Mannheim, Indianapolis, Ind.). The ligation was incubated overnight at 14° C. A 3 µl volume of the ligation mix was then digested with HindIII in a 20 µl reaction to linearize the self-ligated EcoRI fragments between the binding sites of the PCR primers. This linearized DNA was then used as a template in a PCR reaction with 2 divergent primers 17011 and 17012, whose sequences shown below were based on the sequence of the protease gene contained on Clone 1.

17011: 5'-GTAGGTTTTCGGTTGCCCCAACT-GTAATCGC-3' (SEQ ID NO:30)

17012: 5'-GGTCCTACTAGAGATGGACGTATT-AAGCCGG-3' (SEQ ID NO:31)

The amplification was performed using the GeneAmp Kit (Perkin-Elmer, Foster City, Calif.) following the manufacturer's instructions.

The amplification resulted in a 1700 bp PCR product. The 1700 bp product was cloned into pCR2.1 from the TA Cloning Kit and sequenced as previously described. Comparison of the deduced amino acid sequence with the known amino acid sequence of the protease disclosed in JP 4197182 indicated that the cloned inverse PCR product contained the 3' end of the Bacillus JP170 protease gene.

Example 12

Reconstruction of the Bacillus JP170 Protease Gene

Figure 3:
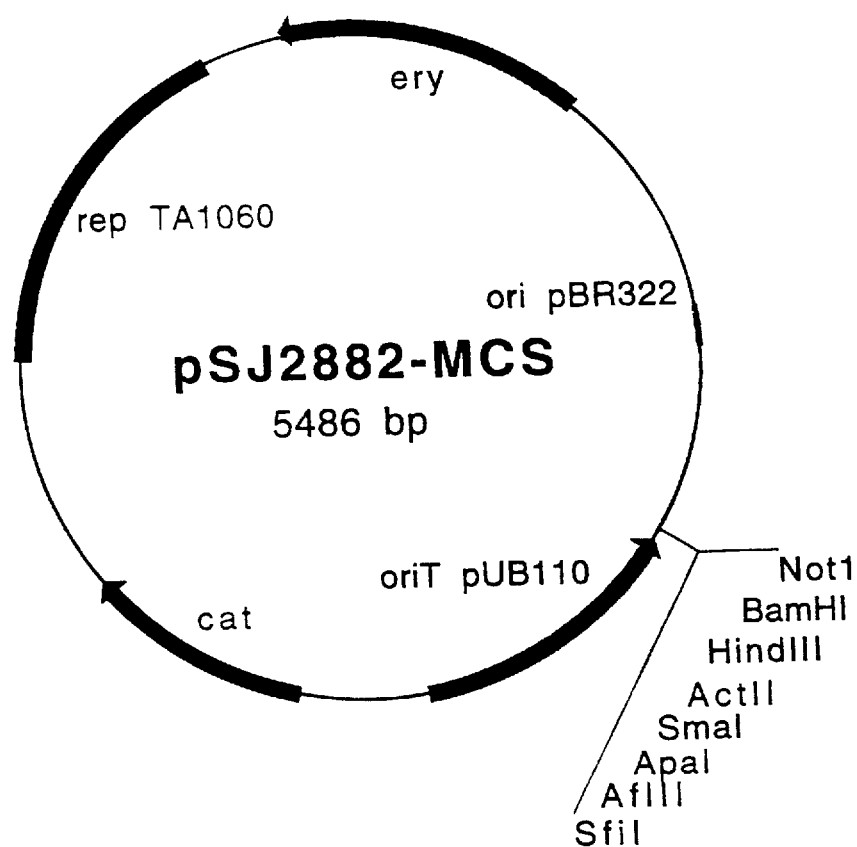
FIG. 3 shows a restriction map of pSJ2882-MCS.

The 5' and 3' ends of the Bacillus JP170 protease gene were cloned into the multicopy Bacillus vector pSJ2882-MCS (FIG. 3) to reconstruct the Bacillus JP170 protease gene. pSJ2882-MCS is derived from pHP13 (Haima et al., 1987, *Molecular General Genetics* 209: 335–342), but contains a SfiI-NotI-flanked MCS, and also a SstI 0.5 kb fragment containing the oriT region from pUB 110. This latter fragment permits mobilization of the plasmid into *Bacillus subtilis* A164 by pLS20-mediated conjugation (Battisti et al., 1985, *Journal of Bacteriology* 162: 543–550).

PCR-amplification from Bacillus JP170 chromosomal DNA with primers adding new restriction sites allowed cloning of the 5' and 3' fragments separately into the plasmid. The following primers were used for the addition of a 5' SmaI site into the 5' Bacillus JP170 protease gene fragment:

170Sma: 5'-CTCCCCCGGGGATGTGTTATAAATTG-AGAGGAG-3' (SEQ ID NO:32)

17030R: 5'-CCTCGTGAAGAGAATTGAGC-AACATGG-3' (SEQ ID NO:33)

The following primers were used for the addition of a 3' NotI site into the 3' Bacillus JP170 protease gene fragment:

17027F: 5'-GCGATTACAGTTGGGGCAACC-3' (SEQ ID NO:34)

17035NOT: 5'-GCGGCCGCGTACTCTCATCAA-TTTCCCAAGC-3' (SEQ ID NO:35)

17036NOT: 5'-GCGGCCGCGTCATAAACGTTGC-AATCGTGCTC-3' (SEQ ID NO:36)

The amplification reactions were performed under the same conditions as described in Example 9.

The 5' end PCR product included a new SmaI site 35 bp upstream of the ATG (including the RBS) and extended past the internal HindIII site. This fragment was cloned as a SmaI-HindIII fragment into the SmaI-HindIII site of pSJ2882-MCS. The 3' end was amplified from the HindIII site to 192 bp downstream of the stop codon, adding a NotI site, and was cloned as a HindIII-NotI fragment downstream of the 5' end.

The amyQ promoter (the promoter of a gene encoding a *Bacillus licheniformis* amylase called BAN™, Novo Nordisk A/S, Bagsvaerd, Denmark) was PCR-amplified using primers 37 and 38 listed below according to the amplification conditions described in Example 9:

Primer 37: 5'-TTTGGCCTTAAGGGCCTGCA ATCGATTGTTTGAGAAAAGAAG-3' (SfiI and ClaI sites underlined, respectively) (SEQ ID NO:37)

Primer 38: 5'-TTTGAGCTCCATCA-TTTTCTTATACAAATTATAACACATATCAG-3' (SstI site underlined) (SEQ ID NO:38)

Figure 4:
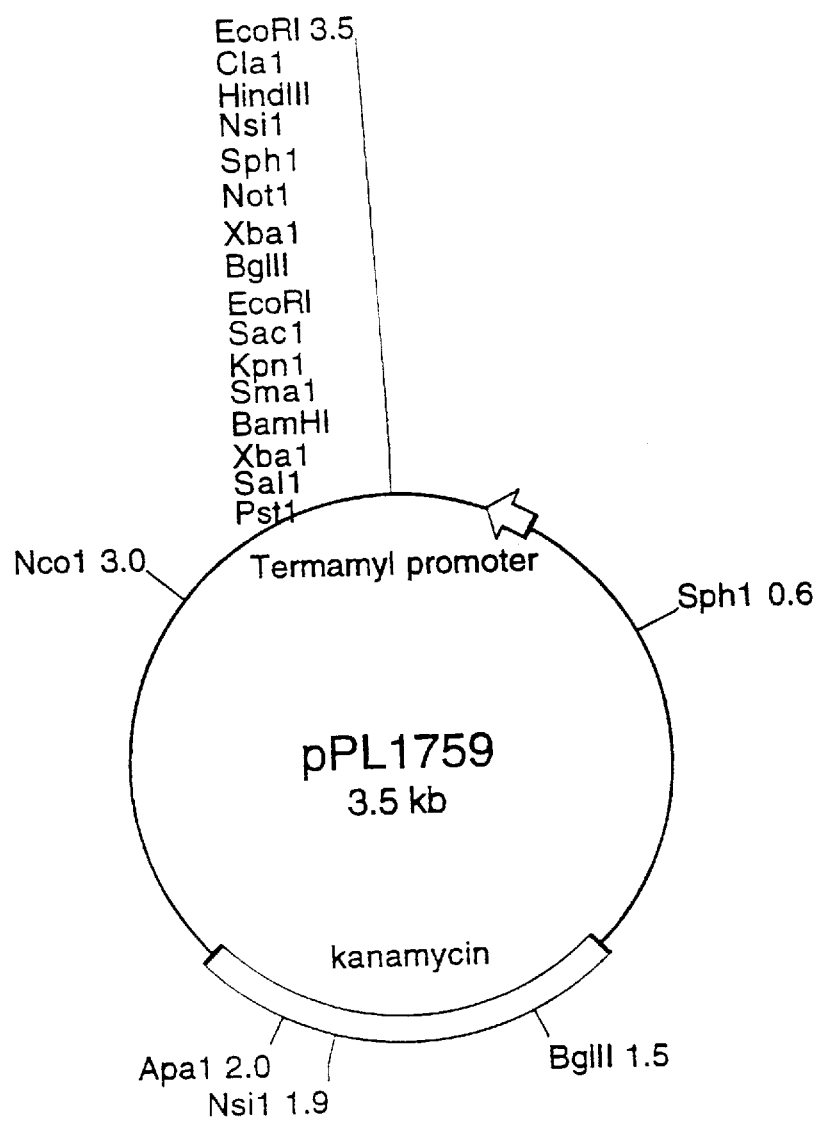
FIG. 4 shows a restriction map of pPL1759.

The amyL promoter (the promoter of a gene encoding a *Bacillus amyloliquefaciens* amylase called TERMAMYL™, Novo Nordisk A/S, Bagsvaerd, Denmark) was PCR amplified as described in Example 9 from pPL1759 (FIG. 4), a pUB 101-based plasmid containing the amyL promoter. Primer term1SFi was used in the amplification to add an SfiI site to the 5' end and primer 2iSfi was used to add a SacI site to the 3' end:

Primer term1SFi: 5'-CCAGGCCTTAAGGGCCGCAT-GCGTCCTCTTTG-3' (SEQ ID NO:39)

Primer 2iSfi: 5'-CCAGAGCTCCTTCAATGTAACATATGA-3' (SEQ ID NO:40)

The amyQ promoter (BAN™ promoter) and amyL promoter (TERMAMYL™ promoter) were then inserted upstream of the reconstructed gene into the SfiI-SmaI sites as SfiI-Ecl136II (blunt) fragments to produce p170BAN and p170TERM, respectively.

Example 13

Sequence Analysis of the Bacillus JP170 Protease Gene

The reconstructed Bacillus JP170 protease gene was sequenced using an Applied Biosystems Model 377 Sequencer according to the manufacturer's instructions.

DNA sequence analysis of the reconstructed protease gene revealed an open reading frame of 1923 bp as shown in FIG. 5 (SEQ ID NO:41). The deduced amino acid sequence (SEQ ID NO:42) as shown in FIG. 5 consists of 641 amino acids including a 33 amino acid signal sequence and a 175 amino acid prepro region. The entire protein, including the signal sequence and prepro region, has 77% identity to the protease disclosed in JP 4197182, and the deduced mature protein has 89% identity to the same protease (FIG. 6, SEQ ID NO:43). Notably, it also contains the C-terminal extension seen in the protease disclosed in JP 4197182. The best homology in the protein database was to subtilisin precursor where the homology was only 35% identity (FIG. 6, SEQ ID NO:44).

Example 14

Transformation of *Bacillus subtilis* with p170BAN and p170TERM

Plasmids p170BAN and p170TERM were transformed into competent cells of *Bacillus subtilis* strain A164Δ5 according to the method of Petit et al., 1990, supra, and selected for chloramphenicol resistance.

Transformants were patched onto TBAB plates containing 5 μg of chloramphenicol per ml and 1% milk and incubated at 37° C. overnight to test for protease production. Strains containing either p170BAN or p170Term made faint halos when compared to strains containing the vector only, which made no halos.

Plasmid p170BAN was also transformed into competent cells of *Bacillus subtilis* strain 168 aprE- nprE- amyE-spoIIE::Tn917 as described above. One transformant designated *Bacillus subtilis* LC20 produced zones on 1% milk-TBAB plates.

Example 15

Integration of pLC20 and pLC21 into *Bacillus subtilis*

Figure 7:
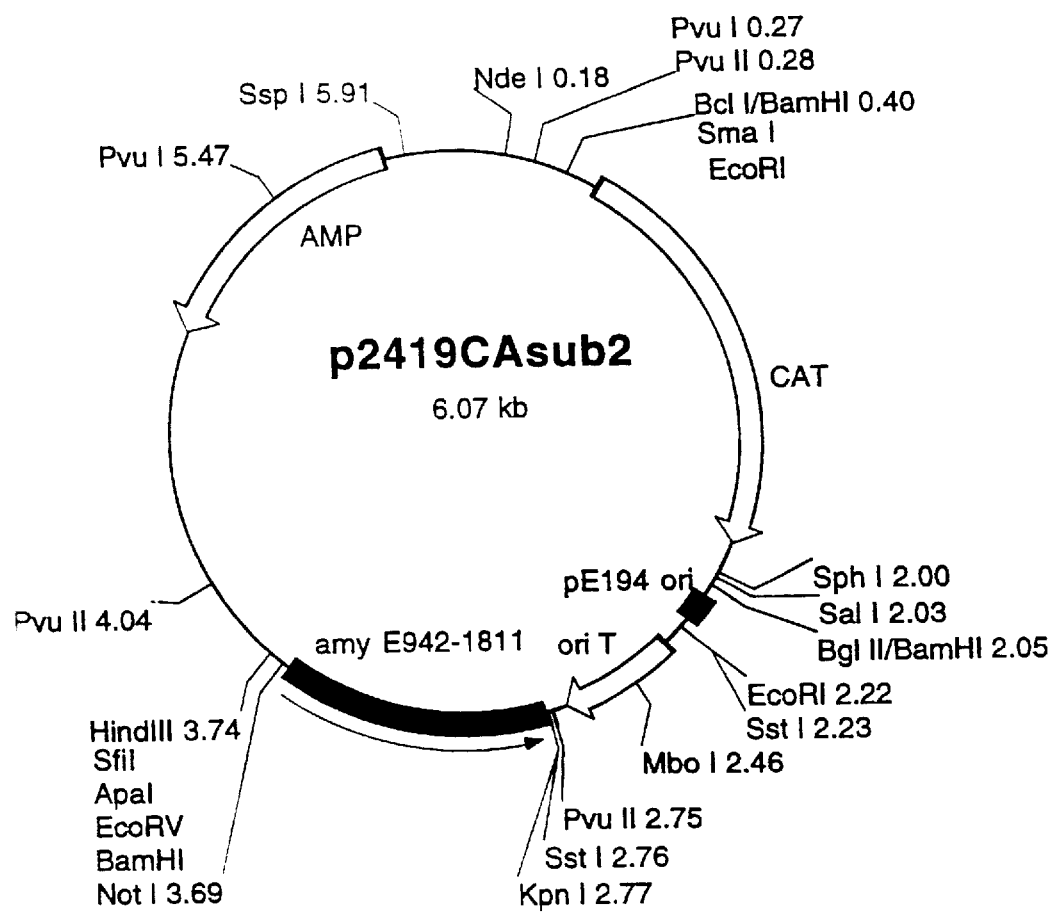
FIG. 7 shows a restriction map of pPL2419.

To construct the integration vector pCAsub2, the neomycin resistance gene of pPL2419 (FIG. 7) was excised by digestion with BclI and BglII and replaced with the chloramphenicol acetyltransferase (cat) gene-containing BamHI fragment from pMI1101 (Youngman et al., 1984, Plasmid 12: 1–9) to create plasmid pPL2419-cat. (BamHI sticky ends are compatible with BclI and BglII sticky ends.) Then, the multiple cloning site (MCS) of pPL2419-cat was replaced with a new MCS containing SfiI and NotI sites created by annealing the two oligonucleotides together shown (SEQ ID NO:45 and SEQ ID NO:46):

5'-<u>AGCTT</u>GGCCTTAAGGGCCCGATATCGGATCC

GCGGCCGCTGCA<u>GGTAC</u>-3' (HindIII and KpnI compatible sites are underlined, SfiI and NotI sites are double-underlined) (SEQ ID NO:45)

5'-CTGCAGCGGCCGCGGATCCGATATCGGGCCC-TTAAGGCCA-3' (SEQ ID NO:46)

Figure 8:
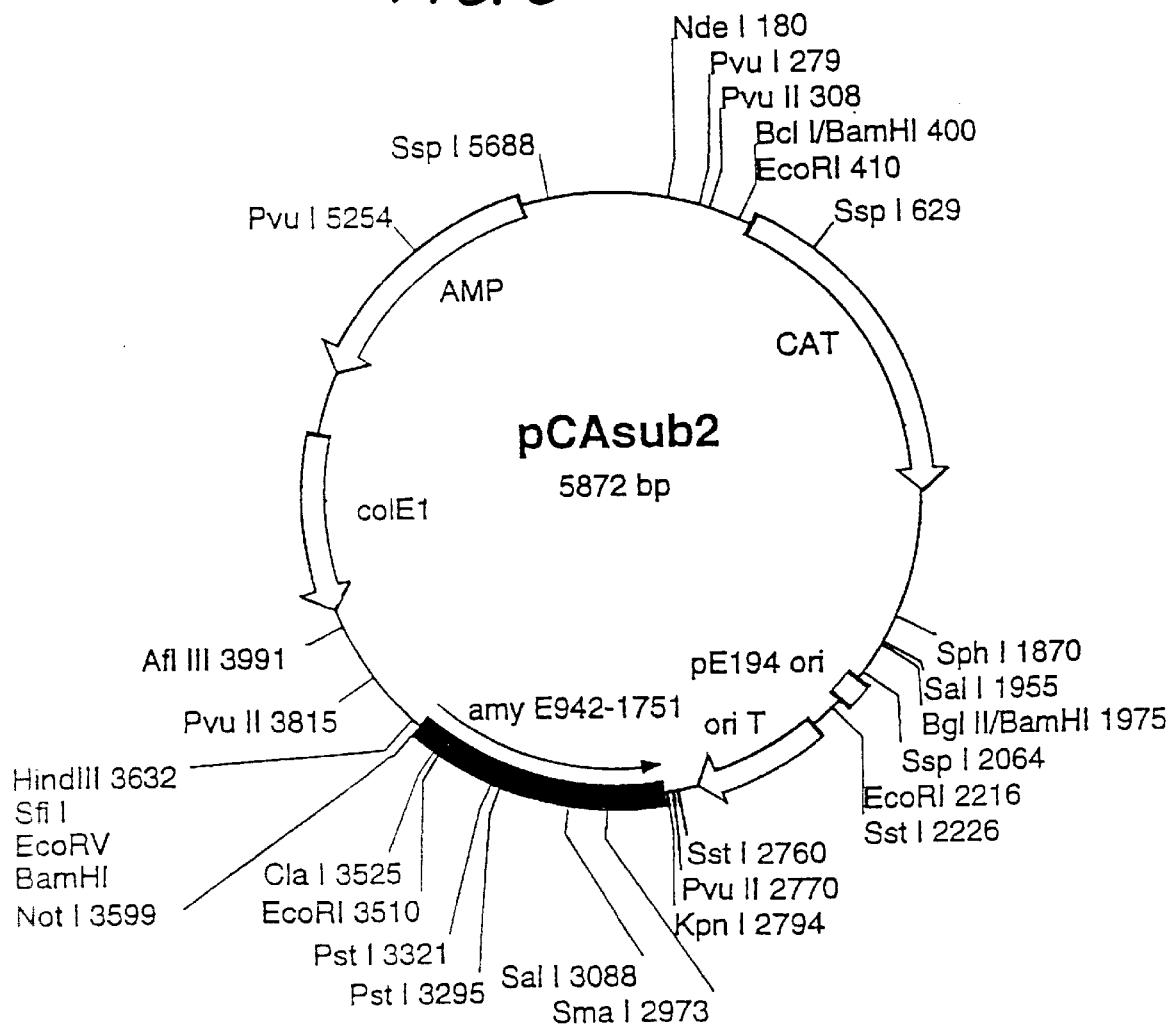
FIG. 8 shows a restriction map of pCAsub2.

The annealed oligonucleotides were ligated to HindIII and KpnI-cut pPL2419-cat to generate p2419MCS5-cat. Then, nucleotides 942 to 1751 of amyE (GenBank Locus BSAMYL, accession numbers V00101, J01547) were PCR-amplified using primers containing NotI and KpnI (Asp718) linkers (SEQ ID NO:47 and SEQ ID NO:48) and *Bacillus subtilis* strain A164Δ5 chromosomal DNA as template, and inserted into NotI and Asp718 -digested p2419MCS5, generating integration vector pCAsub2 (FIG. 8), CAsub referring to <u>c</u>hloramphenicol resistance, <u>a</u>mylase homology, for use in a *subtilis* host.

5'-<u>GCGGCCGC</u>GATTTCCAATGAG-3' (nucleotides added to create Not I site are underlined) (SEQ ID NO:47)

5'-<u>GGTACC</u>TGCATTTGCCAGCAC-3' (nucleotides added to create Asp 718 I site are underlined) (SEQ ID NO:48)

Integration of this vector alone into *Bacillus subtilis* 168 and plating on starch azure overlay plates showed complete elimination of amylase activity.

The amyQ promoter and amyL promoter Bacillus JP170 protease gene cassettes were isolated from the pSJ2882-MCS-based plasmids p170BAN and p170TERM and cloned into the Sfi1-Not1 sites of the Bacillus integration vector pCAsub2 to produce pLC20 and pLC21, respectively. pSJ2882-MCS is unable to replicate independently in Bacillus and therefore must integrate into the chromosome to be stably maintained. It contains a truncated version of the amyE gene which serves as a source of homology, and integration by a single crossover results in insertion of the entire plasmid at the amyE locus.

pLC20 (amyQ promoter) and pLC21 (amyL promoter) were transformed into competent cells of *Bacillus subtilis* strains A164Δ5 and A1630Δ5 according to the method of Petit et al., 1990, supra. The integrants were designated *Bacillus subtilis* A164Δ5-B-JP170, *Bacillus subtilis* A164Δ5-T-JP170, *Bacillus subtilis* A1630Δ5-B-JP170, and *Bacillus subtilis* A1630Δ5-T-JP170 where B is the BAN™ promoter, T is the TERMAMYL™ promoter, and JP170 is the protease gene. Chloramphenicol-resistant transformants of each were tested for protease production on 1% milk-TBAB plates.

All transformants tested made halos that were larger and more distinct than the multicopy pSJ2882MCS-based transformants. The presence of the Bacillus JP170 protease and integration at the amyE locus were verified by PCR as described in Example 16.

Example 16

Integration Screening

Putative integrants described in Example 15 were screened by PCR to verify the presence of the protease gene and to verify integration into the amyE locus. Genomic DNA from the putative integrants was prepared by resuspending a single colony in 100 μl of H$_2$O, freezing in dry ice for 5 minutes, followed by boiling for 5 minutes, then repeating the cycle 3 times. Suspensions were centrifuged for 10 minutes. PCR reactions using 5 μl of supernatant were set up as described in Example 9 using the following protease primers:

17020: 5'-GCTGCACTATTGTCTTCTG-3' (SEQ ID NO:49)

17025: 5'-CAGCAACTGCTACAATCTG-3' (SEQ ID NO:50)

The following primers were used for screening integration:

17037: 5'-GTGCAGGCTTACAATGTACCAG-3' (SEQ ID NO:51)

LCamyREV: 5'-GCATTTACCTGGCTCCAATGATTC-3' (SEQ ID NO:52)

If the protease was present in the strain, then amplification with the protease primers would result in a 665 bp band. If the protease gene was integrated at the amyE locus, then amplification would result in a 1555 bp band using the integration primers.

Agarose gel electrophoresis of the resulting PCR products yielded a 1555 bp band confirming the integration of the Bacillus JP170 protease gene into the chromosome.

Example 17

Amplification of the Bacillus JP170 Protease Gene Expression Cassettes

The amyQ promoter (BAN™ promoter) and amyL promoter TERMAMYL™ promoter) Bacillus JP170 protease gene cassettes were amplified in the integrated strains *Bacillus subtilis* A164Δ5-B-JP170, *Bacillus subtilis* A164Δ5-T-JP170, *Bacillus subtilis* A1630Δ5-B-JP170, and *Bacillus subtilis* A1630Δ5-T-JP170 strains. This was achieved by plating on TBAB plates containing successively higher chloramphenicol concentrations of 15, 30, 45, 60, and 80 μg per ml.

The stability of the protease integration after amplification was confirmed by patching on TBAB plates containing 1% milk at each chloramphenicol concentration. Production of halos showed 100% stability. After a few hours, amplified strains produced halos comparable in size to halos produced overnight by unamplified strains.

Example 18

Copy Number Determination

Southern blots were performed to estimate the copy number of the Bacillus JP170 protease gene expression cassettes in the amplified versus the unamplified versions of *Bacillus subtilis* A164Δ5-T-JP170 and *Bacillus subtilis* A1630Δ5-B-JP170 strains. Genomic DNA prepared from the strains according to the Bacterial DNA Isolation Protocol described in the Qiagen Genomic DNA Handbook (Qiagen, Chatsworth, Calif.) according to the manufacturer's instructions was cut with HindIII, ran on a 0.8% agarose gel, blotted using PosiBlot Pressure Blotter and Pressure Control Station (Stratagene, La Jolla, Calif.), and hybridized and detected using probe 1/291 (Example 9) and the DIG System Hybridization and Detection Kit (Boehringer Mannheim, Indianapolis, Ind.) according to the manufacturers' instructions. Using the Storm Imaging System Model 860 (Molecular Dynamics, Sunnyvale, Calif.) according to the manufacturer's instructions, it was estimated that the cassettes were amplified at least four times in each strain.

The Southern blot of the amplified Bacillus subtilis A164Δ5-T-JP170 showed a 300 bp deletion in the amyL promoter (TERMAMYL™ promoter) Bacillus JP170 protease gene cassette. However, SDS-PAGE analysis using Novex 14% Tris-Glycine Precast Gel-1.0 mm×15 well and Novex DryEase Mini Gel Drying System (Novel Experimental Technology, San Diego, Calif.) according to the manufacturer's instructions showed that the expression of the Bacillus subtilis JP170 protease gene was not affected by this deletion.

Using a series of PCR reactions, it was established that the deletion was 5' of the Bacillus JP170 protease gene and encompasses the amyL promoter. The PCR reactions were performed using several primers described supra and the following primers:

17021: 5'-CCAATAGTAGAAGGACTG-3' (SEQ ID NO:53)
RB1701: 5'-CTTCAGATTGGAAAGCGAGCGG-ACGGAATCATTGATC-3' (SEQ ID NO:54)
RB1702: 5'-CTCAGCTTGAAGAAGTGA-3' (SEQ ID NO:55)
RB1703: 5'-GAAGCAGAGAGGCTATTG-3' (SEQ ID NO:56)
RB1704: 5'-GAAAATATAGGGAAAATGT-3' (SEQ ID NO:57)

The PCR reactions were performed using the following primer pairs: 17037/17036Not, Term1Sf/RB1701, RB1702/17021, RB1703/17021, RB1704/17021, 17036Not/Term1Sfi, 17020/17025, 170Sma/17021, M13-48Rev./17021 with 5 μg of 40 μg/ml template DNA, 2.5 μl 10×PCR buffer (Perkin-Elmer, Foster City, Calif.) containing 15 nM MgCl₂, 1 μl of 10 mM MgCl₂, 5 μl of 1 mM dNTP mix, 2.5 μl of 5 pmol/μl of each primer pair, 0.125 μl of 5 U/μl AmpliTaq Gold polymerase (Perkin-Elmer, Foster City, Calif.), and 6.375 μl of deionized water were used in each PCR reaction. Reactions were incubated in a Stratagene Robocycler 40 programmed for 1 cycle at 96° C. for 10 minutes, 30 cycles each at 96° C. for 1 minute, 55° C. for 1 minute, and 72° C. for 1 minute, and 1 cycle at 72° C. for 5 minutes.

Since the amyL promoter was not present in the amplified Bacillus subtilis A164Δ5-T-JP170, the pUC19 sequence (lacZ promoter) found upstream of the amyL promoter probably served as the driving promoter for the Bacillus JP170 gene.

Reamplification of Bacillus subtilis A164Δ5-T-JP170 by plating on increasing concentrations of chloramphenicol as described in Example 17 was performed in order to obtain a deletion-free promoter/protease cassette. Genomic DNA from Bacillus subtilis A164Δ5-T-JP170 was prepared by resuspending a single colony in 100 μl of deionized water, boiling for 5 minutes, followed by freezing for 5 minutes, then repeating this cycle three times. The suspensions were centrifuged for 10 minutes. The PCR reactions were set up as mentioned above using 5 μl of supernatant as template DNA and the primer pair Term1Sfi/17021. At a chloramphenicol concentration of 20 μg/ml, it was shown that a deletion was present in this newly amplified version.

Retransformation of Bacillus subtilis A164Δ5 with pLC21 was performed in order to obtain a deletion-free promoter/protease cassette. PCR using the primer pair M13-48 Reverse/17021 as described above, it was shown that this unamplified strain was deletion free. This strain was amplified by successive plating on increasing concentrations of chloramphenicol as described in Example 17. PCR reactions using the primer pair M13-48Reverse/17021 showed that the amplified version (up to 40 μg/ml chloramphenicol) was deletion free. However, the deletion-free amplified version was difficult to grow and produced very small halos on 1% milk-TBAB plates when compared to the amplified strain containing the amyL deletion.

The Southern blot of Bacillus subtilis A1630Δ5-B-JP170, using the same protocol as for Bacillus subtilis A164Δ5-T-JP170, did not show any deletion in the promoter/protease cassette.

Example 19

Expression of Bacillus JP170 Protease in Shake Flasks

Bacillus subtilis A164Δ5-B-JP170, Bacillus subtilis A164Δ5-T-JP170, Bacillus subtilis A1630Δ5-B-JP170, and Bacillus subtilis A1630Δ5-T-JP170 strains were cultivated in shake flasks at 37° C. and 250 rpm for 5 days containing 50 ml of PS-1 medium composed of 10% sucrose, 4% soybean flour, 0.42% anhydrous disodium phosphate, and 0.5% calcium carbonate supplemented with 5 μg of chloramphenicol per ml. In addition, Bacillus subtilis A164Δ5::pCAsub2 containing the integration vector was used as a negative control.

The stability of the protease integration was confirmed via casein plating at the beginning and at the end of each assay as described in Example 18. In each instance, the integration was 100% stable as shown by the production of large halos overnight (halos can be observed within a few hours).

SDS-PAGE analysis using Novex Precast Gels as described in Example 18 was performed to determine the expression levels in both assays. When the four strains were compared, it was observed that Bacillus subtilis A164Δ5-T-JP170 expression was greater compared to Bacillus subtilis A164Δ5-B-JP170. The opposite was true for Bacillus subtilis A1630Δ5 strain where expression of Bacillus subtilis A1630Δ5-B-JP170 was greater compared to Bacillus subtilis A1630Δ5-T-JP170. The negative control produced no detectable JP170 protease.

Deposit of Biological Materials

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| Bacillus subtilis LC20 (p170BAN) | NRRL B-21680 | April 4, 1997 |

What is claimed is:

1. An isolated nucleic acid sequence encoding a polypeptide having protease activity comprising an amino acid sequence which has at least 95% identity with the amino acid sequence set forth in SEQ ID NO:42; or an allelic form or a fragment thereof, wherein the fragment retains protease activity.

2. The nucleic acid sequence of claim 1, wherein the nucleic acid sequence encodes an amino acid sequence with at least 95% identity with the amino acid sequence set forth in SEQ ID NO:42; or a fragment thereof, wherein the fragment retains protease activity.

3. The nucleic acid sequence of claim 2, wherein the nucleic acid sequence encodes an amino acid sequence with at least 97% identity with the amino acid sequence set forth in SEQ ID NO:42; or a fragment thereof, wherein the fragment retains protease activity.

4. The nucleic acid sequence of claim 1, wherein the nucleic acid sequence encodes an amino acid sequence comprising the amino acid sequence set forth in SEQ ID NO:42; or a fragment thereof, wherein the fragment retains protease activity.

5. The nucleic acid sequence of claim 4, wherein the nucleic acid sequence encodes an amino acid sequence comprising the amino acid sequence set forth in SEQ ID NO:42.

6. The nucleic acid sequence of claim 4, wherein the nucleic acid sequence encodes an amino acid sequence which has the amino acid sequence set forth in SEQ ID NO:42; or a fragment thereof, wherein the fragment retains protease activity.

7. The nucleic acid sequence of claim 6, wherein the nucleic acid sequence encodes an amino acid sequence which has the amino acid sequence set forth in SEQ ID NO:42.

8. The nucleic acid sequence of claim 7, wherein the nucleic acid sequence is set forth in SEQ ID NO:41.

9. The nucleic acid sequence of claim 2, wherein the nucleic acid sequence is obtained from an alkalophilic Bacillus.

10. The nucleic acid sequence of claim 9, wherein the nucleic acid sequence is obtained from alkalophilic Bacillus NCIB 12513.

11. The nucleic acid sequence of claim 1, which comprises the protease-encoding nucleic acid sequence contained in the plasmid p170BAN which is contained in *Bacillus subtilis* NRRL B-21680.

12. A nucleic acid construct comprising the nucleic acid sequence of claim 1 operably linked to one or more control sequences capable of directing the expression of the polypeptide in a suitable expression host.

13. A recombinant expression vector comprising the nucleic acid construct of claim 12, a promoter, and transcriptional and translational stop signals.

14. The vector according to claim 13, further comprising a selectable marker.

15. A recombinant host cell comprising the nucleic acid construct of claim 12.

16. The cell according to claim 15, wherein the nucleic acid construct is contained on a vector.

17. The cell according to claim 15, wherein the nucleic acid construct is integrated into the host cell genome.

18. The cell according to claim 15, wherein the host cell is a bacterial cell.

19. The cell according to claim 18, wherein the bacterial cell is a Bacillus, Streptomyces, or Pseudomonas cell.

20. The cell according to claim 19, wherein the Bacillus cell is selected from the group consisting of *Bacillus alkalophilus, Bacillus amyloliquefaciens, Bacillus brevis, Bacillus circulans, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis*.

21. A method for producing a polypeptide having protease activity comprising (a) cultivating the host cell of claim 15 under conditions conducive to expression of the polypeptide; and (b) recovering the polypeptide.

\* \* \* \* \*

UNITED STATES PATENT AND TRADEMARK OFFICE
CERTIFICATE OF CORRECTION

PATENT NO. : 5,891,701
DATED : April 6, 1999
INVENTOR(S) : Sloma *et al.*

It is certified that error appears in the above-indentified patent and that said Letters Patent is hereby corrected as shown below:

On the Title Page, Item 73: delete "BioTech" and insert --Biotech--
Col. 60, line 10: delete "Bacillus" and insert --*Bacillus*--
Col. 60, line 10: delete "Streptomyces" and insert --*Streptomyces*--
Col. 60, line 10: delete "Pseudomonas" and insert --*Pseudomonas*--

Signed and Sealed this

Twenty-second Day of May, 2001

*Attest:*

NICHOLAS P. GODICI

*Attesting Officer*  Acting Director of the United States Patent and Trademark Office

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GAGCTCACAG AGATACGTGG GC 22

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GGATCCACAC CAAGTCTGTT CAT 23

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GGATCCGCTG GACTCCGGCT G 21

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

AAGCTTATCT CATCCATGGA AA 22

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

AAGCTTAGGC ATTACAGATC 20

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CGGATCTCCG TCATTTTCCA GCCCGATGCA GCC                33

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GGCTGCATCG GGCTGGAAAA TGACGGAGAT CCG                33

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GATCACATCT TTCGGTGG                18

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

CGTTTATGAG TTTATCAATC                20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

AGACTTCCCA GTTTGCAGGT                20

( 2 ) INFORMATION FOR SEQ ID NO:11:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CAAACTGGGA AGTCTCGACG GTTCATTCTT CTCTC                35

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

TCCAACAGCA TTCCAGGCTG 20

( 2 ) INFORMATION FOR SEQ ID NO:13:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

GCGAATTCTA CCTAAATAGA GATAAAATC 29

( 2 ) INFORMATION FOR SEQ ID NO:14:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

GTTTACCGCA CCTACGTCGA CCCTGTGTAG CCTTGA 36

( 2 ) INFORMATION FOR SEQ ID NO:15:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

TCAAGGCTAC ACAGGGTCGA CGTAGGTGCG GTAAAC 36

( 2 ) INFORMATION FOR SEQ ID NO:16:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

GCAAGCTTGA CAGAGAACAG AGAAGCCAG 29

( 2 ) INFORMATION FOR SEQ ID NO:17:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

CGTCGACGCC TTTGCGGTAG TGGTGCTT 28

( 2 ) INFORMATION FOR SEQ ID NO:18:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:18:

CGCGGCCGCA GGCCCTTAAG GCCAGAACCA AATGAA 36

( 2 ) INFORMATION FOR SEQ ID NO:19:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

TGGCCTTAAG GGCCTGCGGC CGCGATTTCC AATG       34

( 2 ) INFORMATION FOR SEQ ID NO:20:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GAAGCTTCTT CATCATCATT GGCATACG       28

( 2 ) INFORMATION FOR SEQ ID NO:21:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

AAGCTTTGAA TGGGTGTGG       19

( 2 ) INFORMATION FOR SEQ ID NO:22:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

CCGCTTGTTC TTTCATCCCC TGAAACAACT GTACCG       36

( 2 ) INFORMATION FOR SEQ ID NO:23:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

CAGTTGTTTC AGGGGATGAA AGAACAAGCG GCTG       34

( 2 ) INFORMATION FOR SEQ ID NO:24:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

CTGACATGAG GCACTGAC       18

( 2 ) INFORMATION FOR SEQ ID NO:25:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( x i ) SEQUENCE DESCRIPTION: SEQ ID NO:25:

```
Asn  Asp  Val  Ala  Arg  Gly  Ile  Val  Lys  Ala  Asp  Val  Ala  Gln  Asn  Asn
 1              5                        10                       15
Phe  Gly  Leu  Tyr  Gly  Gln  Gly  Gln  Ile  Val  Ala  Asp  Thr  Gly  Leu  Asp
              20                       25                       30
Thr  Gly  Arg  Asn  Asp  Ser
              35
```

( 2 ) INFORMATION FOR SEQ ID NO:26:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( x i ) SEQUENCE DESCRIPTION: SEQ ID NO:26:

```
Gly  Ala  Ala  Asp  Val  Gly  Leu  Gly  Phe  Pro  Asn  Gly  Asn  Gln  Gly  Trp
 1              5                        10                       15
Gly  Arg  Val  Thr  Leu  Asp  Lys
              20
```

( 2 ) INFORMATION FOR SEQ ID NO:27:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

CCCCACCTGT TCCTTGGAAC C       21

( 2 ) INFORMATION FOR SEQ ID NO:28:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

GGATGTAAGC GAGTGCCAAA AATTGG       26

( 2 ) INFORMATION FOR SEQ ID NO:29:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

TAGGCAGGCA ATGTGCGTGC GAACGG       26

( 2 ) INFORMATION FOR SEQ ID NO:30:

( i ) SEQUENCE CHARACTERISTICS:
        ( A ) LENGTH: 31 base pairs ( B ) TYPE: nucleic acid
( C ) STRANDEDNESS: single
( D ) TOPOLOGY: linear ( x i ) SEQUENCE DESCRIPTION: SEQ ID NO:30:

GTAGGTTTTC GGTTGCCCCA ACTGTAATCG C 31

( 2 ) INFORMATION FOR SEQ ID NO:31:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:31:

GGTCCTACTA GAGATGGACG TATTAAGCCG G 31

( 2 ) INFORMATION FOR SEQ ID NO:32:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:32:

CTCCCCCGGG GATGTGTTAT AAATTGAGAG GAG 33

( 2 ) INFORMATION FOR SEQ ID NO:33:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:33:

CCTCGTGAAG AGAATTGAGC AACATGG 27

( 2 ) INFORMATION FOR SEQ ID NO:34:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:34:

GCGATTACAG TTGGGGCAAC C 21

( 2 ) INFORMATION FOR SEQ ID NO:35:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:35:

GCGGCCGCGT ACTCTCATCA ATTTCCCAAG C 31

( 2 ) INFORMATION FOR SEQ ID NO:36:

( i ) SEQUENCE CHARACTERISTICS:
( A ) LENGTH: 32 base pairs
( B ) TYPE: nucleic acid
( C ) STRANDEDNESS: single -continued ( D ) TOPOLOGY: linear ( x i ) SEQUENCE DESCRIPTION: SEQ ID NO:36:

GCGGCCGCGT CATAAACGTT GCAATCGTGC TC                                                        32

( 2 ) INFORMATION FOR SEQ ID NO:37:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

TTTGGCCTTA AGGGCCTGCA ATCGATTGTT TGAGAAAAGA AG                                              42

( 2 ) INFORMATION FOR SEQ ID NO:38:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

TTTGAGCTCC ATTTTCTTAT ACAAATTATA TTTACATAT CAG                                              43

( 2 ) INFORMATION FOR SEQ ID NO:39:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

CCAGGCCTTA AGGGCCGCAT GCGTCCTTCT TTG                                                        33

( 2 ) INFORMATION FOR SEQ ID NO:40:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

CCAGAGCTCC TTTCAATGTA ACATATGA                                                              28

( 2 ) INFORMATION FOR SEQ ID NO:41:

( i ) SEQUENCE CHARACTERISTICS:
        ( A ) LENGTH: 3003 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:41:

CTTAGGCAAG CTTTACTCTA TACAGAGATT ACATCCTCAA GCCATTGAAG AATTCGAAAA      60

AAGTTATTAT TTAAAAGAGG ATAGGGGTT AGACAGTAAA TTAAATTCGA TTTATTGTCT      120

TTTGATGGAA TACGATAACA TGGAAGATTC TACTCAATGT AGAAAATGGT TAGAAATTGG      180

GAAATCTTTG CTAACTAGTC CAGACGAATT GGTAGAATAT CATTATTATT TCACCATTTT      240

TGACTATGTC CTAGCAGACA ATATGGATGA GCTTGATGTC TATTTCCAAG AAGTCGTTTT      300

-continued

```
ACCTTTTTTC AACAACAAGA TTTAAAAGAA CCAATTATTA AATATGCAGA GAGGCTCGCC    360
ATCTATTTTG AATCTTGTTA TAAATACAAA AAAGCAAGCT ACTACTATTC GTTATGCTAC    420
CAAGAAATTA AAGAACAAAC TTTTTTATAC TAAGGGGAGG GTAATATGAA AAAAAAACTG    480
TTGCTTGTAG TTTTAGTTGG AATTCTTTTT TTAGTAGGTA CTTTGGAAAA ATCTATTCAA    540
GAGCCTCAAG TAATTGCACA TGGCGAGGTT ACTGCTTTAA AAGATGAACA TCCTGAGCCG    600
CTTCCAAATG GTTAAAAACA ATAAGAACT  TTCTCTACTG GAGAGGGTTC TTTTTTTCTT    660
TCATTTTTTT AGAAATATT  GAATGGTCGC TGTAGTCTGG CTTGACAGTA ATTTTCCATT    720
GGGAAAGTAT GAGCCCAAAA AGCGAATTAT GAAGCTATTT TAATCTGAAT TTTCCCAATA    780
TAAAGTTTTT GTTTCCTGTG ATAAATTAAT GATGTGTTAT AAATTGAGAG GAGTTGAGCT    840
ATAGAATGAG AAAGAAAGGA TCGAAGAGGG TTTTTTTATC CGTTTTATCA GTTGCTGCAC    900
TATTGTCTTC TGTTGCTTTA AGCAGTCCTT CTACTATTGG GGCGAACAAT TTTGAATTGG    960
ACTTTAAGGG GATAGAGACA CTTACGCTAG AGAAGGCTGC CACCAAGCAA GGAAAAACGG   1020
GAAAGGCATC TTTTCTTGTA AACTCTGAAA ATGTGAAAAT CCCAAAGAGT ATTCAAAAGA   1080
AACTAGAAGT AGTTCCAGCG GATAACAAGC TATATATCGT TCAATTTGAC GGACCTATTT   1140
TAGAGGAAAC GCAACTTCAA CTAGAGAAGA CGGGAGCGAA AATTCTCGAT TACATACCAG   1200
ATTACGCTTA TATTGTCGAA TATGATGGGG ATGTAAAGGC CGTAACTAAC GCAATTGCGC   1260
ATTTGGAATC GGTTGAACCA TATTTACCTT TATATAAAAT AGACCCGCAA TTATTTTCCA   1320
GAGGAGCTTC TGAATTAGTA GAAACAGTAG CTTTAGATAA AAAGCAAAGA AGTAAAGAAG   1380
TACGTTTAAG AGGATTGGAA CAAATTGCCC AATACGCGAC AAATAATGAT GTATTATACG   1440
TAACCCCAAA GCCTGAATAC GAAGTTTTGA ATGACGTGGC CCGTGGCATT GTGAAAGCAG   1500
ACGTCGCACA AATAACTTT  GGCTTATATG GACAAGGACA GATTGTAGCA GTTGCTGATA   1560
CTGGGCTTGA TACAGGAAGA AATGACAGTT CGATGCATGA AGCATTCCGC GGTAAGATTA   1620
CCGCACTATA TGCACTGGGC AGAACGAATA ACGCCAATGA TCCAAATGGA CATGGAACCC   1680
ATGTTGCTGG ATCTGTGTTA GGAAATGCTA CAAATAAAGG GATGGCACCG CAAGCCAATC   1740
TAGTCTTTCA ATCTATTATG GATAGTGGTG GAGGGCTGGG AGGACTACCT GCTAATCTAC   1800
AAACATTATT CAGTCAAGCA TATAGTGCTG GAGCGAGAAT TCATACGAAT TCATGGGGGG   1860
CTCCAGTAAA CGGTGCCTAT ACGACAGACT CTCGAAATGT TGATGATTAT GTGAGAAAAA   1920
ATGATATGAC GATTCTTTTT GCGGCCGGAA ATGAGGGACC AGGTAGCGGT ACAATCAGTG   1980
CACCAGGAAC AGCAAAAAAT GCGATTACAG TTGGGGCAAC CGAAAACCTA CGTCCAAGCT   2040
TCGGATCTTA TGCGGATAAT ATTAACCATG TTGCTCAATT CTCTTCACGA GGTCCTACTA   2100
GAGATGGACG TATTAAGCCG GACGTCATGG CACCAGGTAC GTATATTCTC TCTGCTAGAT   2160
CATCATTAGC TCCAGATTCC TCATTCTGGG CAAACCATGA TAGTAAATAT GCCTACATGG   2220
GTGGTACTTC TATGGCTACT CCAATTGTAG CAGGTAATGT TGCACAATTA AGGGAGCATT   2280
TTGTGAAAAA TAGAGGGTA  ACTCCTAAGC CTTCCCTTTT AAAAGCTGCT TTAATTGCAG   2340
GTGCTGCGGA TGTTGGACTT GGCTTTCCAA ATGGTAACCA AGGATGGGGA AGAGTAACGT   2400
TAGATAAATC CCTAAATGTC GCATTTGTGA ATGAAACGAG CCCTTATCA  ACAAGTCAAA   2460
AAGCAACATA TTCGTTTACG GCTCAAGCTG GTAAACCCTT AAAAATATCA CTTGTTTGGT   2520
CAGATGCACC AGGTAGCACG ACGGCATCAC TAACTTTAGT GAATGATTTA GACTTAGTAA   2580
TCACTGCACC AAATGGAACT AAATACGTCG GAAATGACTT TACAGCACCG TATGATAACA   2640
ATTGGGATGG CAGAAACAAC GTGGAAAATG TGTTTATCAA TGCTCCTCAA AGCGGAACGT   2700
```

```
ATACAGTCGA  AGTGCAGGCT  TACAATGTAC  CAGTAAGTCC  GCAAACCTTT  TCTTTAGCGA    2760

TTGTACATTA  AAATATTGGA  AGGAAGAGTT  GTTGATGAAT  ATATCAGCAG  CTCTTTTTTT    2820

GATTAAGCTC  TTTTCGTAAA  GGTTGTTGCT  TTAAGTCGGT  AAAAAGTCGG  TATTTGGACT    2880

TTTTACCAGT  CATTTGCTT   GGGAAATTGA  TGAGAGTACT  TTCATTACTG  ATGGAAAAGA    2940

GCACGATTGC  AACGTTTATG  ACGGGGTGAT  TTCTATTTAC  GAAAAGCAAC  AAAGTATGCG    3000

AAA                                                                      3003
```

( 2 ) INFORMATION FOR SEQ ID NO:42:

( i ) SEQUENCE CHARACTERISTICS:
        ( A ) LENGTH: 641 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:42:

```
Met  Arg  Lys  Lys  Gly  Ser  Lys  Arg  Val  Phe  Leu  Ser  Val  Leu  Ser  Val
 1              5                        10                       15

Ala  Ala  Leu  Leu  Ser  Ser  Val  Ala  Leu  Ser  Ser  Pro  Ser  Thr  Ile  Gly
              20                       25                       30

Ala  Asn  Asn  Phe  Glu  Leu  Asp  Phe  Lys  Gly  Ile  Glu  Thr  Leu  Thr  Leu
         35                       40                       45

Glu  Lys  Ala  Ala  Thr  Lys  Gln  Gly  Lys  Thr  Gly  Lys  Ala  Ser  Phe  Leu
     50                       55                       60

Val  Asn  Ser  Glu  Asn  Val  Lys  Ile  Pro  Lys  Ser  Ile  Gln  Lys  Lys  Leu
65                      70                       75                       80

Glu  Val  Val  Pro  Ala  Asp  Asn  Lys  Leu  Tyr  Ile  Val  Gln  Phe  Asp  Gly
              85                       90                       95

Pro  Ile  Leu  Glu  Glu  Thr  Gln  Leu  Gln  Leu  Glu  Lys  Thr  Gly  Ala  Lys
              100                      105                      110

Ile  Leu  Asp  Tyr  Ile  Pro  Asp  Tyr  Ala  Tyr  Ile  Val  Glu  Tyr  Asp  Gly
              115                      120                      125

Asp  Val  Lys  Ala  Val  Thr  Asn  Ala  Ile  Ala  His  Leu  Glu  Ser  Val  Glu
     130                      135                      140

Pro  Tyr  Leu  Pro  Leu  Tyr  Lys  Ile  Asp  Pro  Gln  Leu  Phe  Ser  Arg  Gly
145                      150                      155                      160

Ala  Ser  Glu  Leu  Val  Glu  Thr  Val  Ala  Leu  Asp  Lys  Lys  Gln  Arg  Ser
              165                      170                      175

Lys  Glu  Val  Arg  Leu  Arg  Gly  Leu  Glu  Gln  Ile  Ala  Gln  Tyr  Ala  Thr
              180                      185                      190

Asn  Asn  Asp  Val  Leu  Tyr  Val  Thr  Pro  Lys  Pro  Glu  Tyr  Glu  Val  Leu
              195                      200                      205

Asn  Asp  Val  Ala  Arg  Gly  Ile  Val  Lys  Ala  Asp  Val  Ala  Gln  Asn  Asn
     210                      215                      220

Phe  Gly  Leu  Tyr  Gly  Gln  Gly  Gln  Ile  Val  Ala  Val  Ala  Asp  Thr  Gly
225                      230                      235                      240

Leu  Asp  Thr  Gly  Arg  Asn  Asp  Ser  Ser  Met  His  Glu  Ala  Phe  Arg  Gly
              245                      250                      255

Lys  Ile  Thr  Ala  Leu  Tyr  Ala  Leu  Gly  Arg  Thr  Asn  Asn  Ala  Asn  Asp
              260                      265                      270

Pro  Asn  Gly  His  Gly  Thr  His  Val  Ala  Gly  Ser  Val  Leu  Gly  Asn  Ala
```

|       |     |     |     |     | 275 |     |     |     |     | 280 |     |     |     |     | 285 |     |     |
|-------|-----|-----|-----|-----|-----|-----|-----|-----|-----|-----|-----|-----|-----|-----|-----|-----|-----|

Thr Asn Lys Gly Met Ala Pro Gln Ala Asn Leu Val Phe Gln Ser Ile
290                     295                 300

Met Asp Ser Gly Gly Leu Gly Gly Leu Pro Ala Asn Leu Gln Thr
305             310              315                       320

Leu Phe Ser Gln Ala Tyr Ser Ala Gly Ala Arg Ile His Thr Asn Ser
              325              330                       335

Trp Gly Ala Pro Val Asn Gly Ala Tyr Thr Thr Asp Ser Arg Asn Val
              340              345              350

Asp Asp Tyr Val Arg Lys Asn Asp Met Thr Ile Leu Phe Ala Ala Gly
        355              360              365

Asn Glu Gly Pro Gly Ser Gly Thr Ile Ser Ala Pro Gly Thr Ala Lys
370                    375              380

Asn Ala Ile Thr Val Gly Ala Thr Glu Asn Leu Arg Pro Ser Phe Gly
385                    390              395                       400

Ser Tyr Ala Asp Asn Ile Asn His Val Ala Gln Phe Ser Ser Arg Gly
              405              410                   415

Pro Thr Arg Asp Gly Arg Ile Lys Pro Asp Val Met Ala Pro Gly Thr
              420              425              430

Tyr Ile Leu Ser Ala Arg Ser Ser Leu Ala Pro Asp Ser Ser Phe Trp
              435              440              445

Ala Asn His Asp Ser Lys Tyr Ala Tyr Met Gly Gly Thr Ser Met Ala
450                    455              460

Thr Pro Ile Val Ala Gly Asn Val Ala Gln Leu Arg Glu His Phe Val
465                    470              475                       480

Lys Asn Arg Gly Val Thr Pro Lys Pro Ser Leu Leu Lys Ala Ala Leu
              485              490                   495

Ile Ala Gly Ala Ala Asp Val Gly Leu Gly Phe Pro Asn Gly Asn Gln
              500              505              510

Gly Trp Gly Arg Val Thr Leu Asp Lys Ser Leu Asn Val Ala Phe Val
              515              520              525

Asn Glu Thr Ser Pro Leu Ser Thr Ser Gln Lys Ala Thr Tyr Ser Phe
530                    535              540

Thr Ala Gln Ala Gly Lys Pro Leu Lys Ile Ser Leu Val Trp Ser Asp
545              550              555                       560

Ala Pro Gly Ser Thr Thr Ala Ser Leu Thr Leu Val Asn Asp Leu Asp
              565              570              575

Leu Val Ile Thr Ala Pro Asn Gly Thr Lys Tyr Val Gly Asn Asp Phe
              580              585              590

Thr Ala Pro Tyr Asp Asn Trp Asp Gly Arg Asn Asn Val Glu Asn
              595              600              605

Val Phe Ile Asn Ala Pro Gln Ser Gly Thr Tyr Thr Val Glu Val Gln
610              615              620

Ala Tyr Asn Val Pro Val Ser Pro Gln Thr Phe Ser Leu Ala Ile Val
625              630              635                       640

His ( 2 ) INFORMATION FOR SEQ ID NO:43:

( i ) SEQUENCE CHARACTERISTICS:
        ( A ) LENGTH: 635 amino acids
        ( B ) TYPE: amino acid
        ( C ) STRANDEDNESS: single
        ( D ) TOPOLOGY: linear ( x i ) SEQUENCE DESCRIPTION: SEQ ID NO:43:

| | | | | | | | | | | | | | | |
|---|---|---|---|---|---|---|---|---|---|---|---|---|---|---|
| Met<br>1 | Lys | Gly | Lys | Lys<br>5 | Arg | Val | Val | Leu | Ser<br>10 | Val | Val | Ala | Ser | Ala<br>15 | Ala |
| Ile | Leu | Ala | Ser<br>20 | Val | Met | Val | Ser | Ser<br>25 | Pro | Thr | Ser | Gly | Ala<br>30 | Asp | Phe |
| Gln | Val | Asn<br>35 | Phe | Asn | Gly | Val | Lys<br>40 | Ser | Leu | Glu | Asn | Ala<br>45 | Ser | Leu | Val |
| Lys | Pro<br>50 | Ile | Ser | Ser | Gly<br>55 | Glu | Ala | Ser | Phe | Leu<br>60 | Val | Asp | Thr | Glu | Asn |
| Ile<br>65 | Asn | Ile | Pro | Lys | Gly<br>70 | Ile | Gln | Lys | Lys<br>75 | Leu | Glu | Ala | Val | Gln | Lys<br>80 |
| Asp | Asn | Glu | Leu | Tyr<br>85 | Ile | Val | Gln | Phe | Thr<br>90 | Gly | Pro | Ile | Ser | Glu<br>95 | Glu |
| Glu | Arg | Lys | Gly<br>100 | Leu | Glu | Ser | Leu | Gly<br>105 | Val | Ser | Ile | Leu | Asp<br>110 | Tyr | Val |
| Pro | Asp | Tyr<br>115 | Ala | Phe | Ile | Val | Gln<br>120 | Tyr | Ser | Gly | Ala | Thr<br>125 | Lys | Asn | Ile |
| Ser | Thr<br>130 | Leu | His | Ser | Val | Glu<br>135 | Asn | Val | Gln | Pro | Phe<br>140 | Leu | Pro | Leu | Tyr |
| Lys<br>145 | Ile | Asp | Pro | Glu | Leu<br>150 | Leu | Thr | Lys | Gly | Ala<br>155 | Ser | Gln | Leu | Val | Gln<br>160 |
| Ala | Val | Ile | Leu | Asn<br>165 | Thr | Lys | His | Glu | Asn<br>170 | Lys | Asn | Met | Lys | Phe<br>175 | Thr |
| Gly | Leu | Asp | Glu<br>180 | Ile | Val | Gln | Tyr | Ala<br>185 | Ala | Asn | Asn | Asp | Val<br>190 | Leu | Tyr |
| Ile | Ser | Pro<br>195 | Lys | Pro | Glu | Tyr | Glu<br>200 | Leu | Met | Asn | Asp | Val<br>205 | Ala | Arg | Gly |
| Ile | Val<br>210 | Lys | Ala | Asp | Val | Ala<br>215 | Gln | Asn | Asn | Tyr | Gly<br>220 | Leu | Tyr | Gly | Gln |
| Gly<br>225 | Gln | Leu | Val | Ala | Val<br>230 | Ala | Asp | Thr | Gly | Leu<br>235 | Asp | Thr | Gly | Arg | Asn<br>240 |
| Asp | Ser | Ser | Met | His<br>245 | Glu | Ala | Phe | Arg | Gly<br>250 | Lys | Ile | Thr | Ala | Leu<br>255 | Tyr |
| Ala | Leu | Gly | Arg<br>260 | Thr | Asn | Asn | Ala | Ser<br>265 | Asp | Pro | Asn | Gly | His<br>270 | Gly | Thr |
| His | Val | Ala<br>275 | Gly | Ser | Val | Leu | Gly<br>280 | Asn | Ala | Leu | Asn | Lys<br>285 | Gly | Met | Ala |
| Pro | Gln<br>290 | Ala | Asn | Leu | Val | Phe<br>295 | Gln | Ser | Ile | Met | Asp<br>300 | Ser | Ser | Gly | Gly |
| Leu<br>305 | Gly | Gly | Leu | Pro | Ser<br>310 | Asn | Leu | Asn | Thr | Leu<br>315 | Phe | Ser | Gln | Ala | Trp<br>320 |
| Asn | Ala | Gly | Ala | Arg<br>325 | Ile | His | Thr | Asn | Ser<br>330 | Trp | Gly | Ala | Pro | Val<br>335 | Asn |
| Gly | Ala | Tyr | Thr<br>340 | Ala | Asn | Ser | Arg | Gln<br>345 | Val | Asp | Glu | Tyr | Val<br>350 | Arg | Asn |
| Asn | Asp | Met<br>355 | Thr | Val | Leu | Phe | Ala<br>360 | Ala | Gly | Asn | Glu | Gly<br>365 | Pro | Asn | Ser |
| Gly | Thr<br>370 | Ile | Ser | Ala | Pro | Gly<br>375 | Thr | Ala | Lys | Asn | Ala<br>380 | Ile | Thr | Val | Gly |
| Ala<br>385 | Thr | Glu | Asn | Tyr | Arg<br>390 | Pro | Ser | Phe | Gly | Ser<br>395 | Ile | Ala | Asp | Asn | Pro<br>400 |
| Asn | His | Ile | Ala | Gln<br>405 | Phe | Ser | Ser | Arg | Gly<br>410 | Ala | Thr | Arg | Asp | Gly<br>415 | Arg |
| Ile | Lys | Pro | Asp | Val | Thr | Ala | Pro | Gly | Thr | Phe | Ile | Leu | Ser | Ala | Arg |

|     |     |     |     |     | 420 |     |     |     |     | 425 |     |     |     |     | 430 |     |     |
| --- | --- | --- | --- | --- | --- | --- | --- | --- | --- | --- | --- | --- | --- | --- | --- | --- | --- |
| Ser | Ser | Leu 435 | Ala | Pro | Asp | Ser | Ser 440 | Phe | Trp | Ala | Asn | Tyr 445 | Asn | Ser | Lys |
| Tyr | Ala 450 | Tyr | Met | Gly | Gly | Thr 455 | Ser | Met | Ala | Thr | Pro 460 | Ile | Val | Ala | Gly |
| Asn 465 | Val | Ala | Gln | Leu | Arg 470 | Glu | His | Phe | Ile | Lys 475 | Asn | Arg | Gly | Ile | Thr 480 |
| Pro | Lys | Pro | Ser | Leu 485 | Ile | Lys | Ala | Ala | Leu 490 | Ile | Ala | Gly | Ala | Thr 495 | Asp |
| Val | Gly | Leu | Gly 500 | Tyr | Pro | Ser | Gly | Asp 505 | Gln | Gly | Trp | Gly | Arg 510 | Val | Thr |
| Leu | Asp | Lys 515 | Ser | Leu | Asn | Val | Ala 520 | Tyr | Val | Asn | Glu | Ala 525 | Thr | Ala | Leu |
| Ala | Thr 530 | Gly | Gln | Lys | Ala | Thr 535 | Tyr | Ser | Phe | Gln | Ala 540 | Gln | Ala | Gly | Lys |
| Pro 545 | Leu | Lys | Ile | Ser | Leu 550 | Val | Trp | Thr | Asp | Ala 555 | Pro | Gly | Ser | Thr | Thr 560 |
| Ala | Ser | Tyr | Thr | Leu 565 | Val | Asn | Asp | Leu | Asp 570 | Leu | Val | Ile | Thr | Ala 575 | Pro |
| Asn | Gly | Gln | Lys 580 | Tyr | Val | Gly | Asn | Asp 585 | Phe | Ser | Tyr | Pro | Tyr 590 | Asp | Asn |
| Asn | Trp | Asp 595 | Gly | Arg | Asn | Asn | Val 600 | Glu | Asn | Val | Phe | Ile 605 | Asn | Ala | Pro |
| Gln | Ser | Gly 610 | Thr | Tyr | Ile | Ile 615 | Glu | Val | Gln | Ala | Tyr 620 | Asn | Val | Pro | Ser |
| Gly 625 | Pro | Gln | Arg | Phe | Ser 630 | Leu | Ala | Ile | Val | His 635 |

( 2 ) INFORMATION FOR SEQ ID NO:44:

( i ) SEQUENCE CHARACTERISTICS:
    ( A ) LENGTH: 418 amino acids
    ( B ) TYPE: amino acid
    ( C ) STRANDEDNESS: single
    ( D ) TOPOLOGY: linear ( x i ) SEQUENCE DESCRIPTION: SEQ ID NO:44:

| Met 1 | Lys | Arg | Ser | Gly 5 | Lys | Ile | Phe | Thr | Thr 10 | Ala | Met | Leu | Ala | Val 15 | Thr |
| --- | --- | --- | --- | --- | --- | --- | --- | --- | --- | --- | --- | --- | --- | --- | --- |
| Leu | Met | Met | Pro 20 | Ala | Ile | Gly | Val | Ser 25 | Ala | Asn | Arg | Gly | Asn 30 | Ala | Ala |
| Asp | Gly | Asn 35 | Glu | Lys | Phe | Arg | Val 40 | Leu | Val | Asp | Ser | Ala 45 | Asn | Gln | Asn |
| Asn | Leu 50 | Lys | Asn | Val | Lys | Glu 55 | Gln | Tyr | Gly | Val | His 60 | Trp | Asp | Phe | Ala |
| Gly 65 | Glu | Gly | Phe | Thr | Thr 70 | Asn | Met | Asn | Glu | Lys 75 | Gln | Phe | Asn | Ala | Leu 80 |
| Gln | Asn | Asn | Lys | Asn 85 | Leu | Thr | Val | Glu | Lys 90 | Val | Pro | Glu | Leu | Glu 95 | Ile |
| Ala | Thr | Ala | Thr 100 | Asn | Lys | Pro | Glu | Ala 105 | Leu | Tyr | Asn | Ala | Met 110 | Ala | Ala |
| Ser | Gln | Ser 115 | Thr | Pro | Trp | Gly | Ile 120 | Lys | Ala | Ile | Tyr | Asn 125 | Ser | Asn |
| Leu | Thr | Ser 130 | Thr | Ser | Gly | Gly 135 | Ala | Gly | Ile | Asn | Ile 140 | Ala | Val | Leu | Asp |
| Thr | Gly | Val | Asn | Thr | Asn | His | Pro | Asp | Leu | Ser | Asn | Asn | Val | Glu | Gln |

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |

Cys Lys Asp Phe Thr Val Gly Thr Asn Phe Thr Asp Asn Ser Cys Thr
              165             170             175

Asp Arg Gln Gly His Gly Thr His Val Ala Gly Ser Ala Leu Ala Asn
            180             185             190

Gly Gly Thr Gly Ser Gly Val Tyr Gly Val Ala Pro Glu Ala Asp Leu
            195             200             205

Trp Ala Tyr Lys Val Leu Gly Asp Asp Gly Ser Gly Tyr Ala Asp Asp
        210             215             220

Ile Ala Glu Ala Ile Arg His Ala Gly Asp Gln Ala Thr Ala Leu Asn
225             230             235             240

Thr Lys Val Val Ile Asn Met Ser Leu Gly Ser Ser Gly Glu Ser Ser
              245             250             255

Leu Ile Thr Asn Ala Val Asp Tyr Ala Tyr Asp Lys Gly Val Leu Ile
            260             265             270

Ile Ala Ala Ala Gly Asn Ser Gly Pro Lys Pro Gly Ser Ile Gly Tyr
        275             280             285

Pro Gly Ala Leu Val Asn Ala Val Ala Val Ala Ala Leu Glu Asn Thr
        290             295             300

Ile Gln Asn Gly Thr Tyr Arg Val Ala Asp Phe Ser Ser Arg Gly His
305             310             315             320

Lys Thr Ala Gly Asp Tyr Val Ile Gln Lys Gly Asp Val Glu Ile Ser
              325             330             335

Ala Pro Gly Ala Ala Val Tyr Ser Thr Trp Phe Asp Gly Gly Tyr Ala
            340             345             350

Thr Ile Ser Gly Thr Ser Met Ala Ser Pro His Ala Ala Gly Leu Ala
            355             360             365

Ala Lys Ile Trp Ala Gln Ser Pro Ala Ala Ser Asn Val Asp Val Arg
        370             375             380

Gly Glu Leu Gln Thr Arg Ala Ser Val Asn Asp Ile Leu Ser Gly Asn
385             390             395             400

Ser Ala Gly Ser Gly Asp Asp Ile Ala Ser Gly Phe Gly Phe Ala Lys
            405             410             415

Val Gln ( 2 ) INFORMATION FOR SEQ ID NO:45:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

AGCTTGGCCT TAAGGGCCCG ATATCGGATC CGCGGCCGCT GCAGGTAC　　　　　　　　　48

( 2 ) INFORMATION FOR SEQ ID NO:46:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

CTGCAGCGGC CGCGGATCCG ATATCGGGCC CTTAAGGCCA　　　　　　　　　　　　　40

( 2 ) INFORMATION FOR SEQ ID NO:47:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:47:

GCGGCCGCGA TTTCCAATGA G 21

( 2 ) INFORMATION FOR SEQ ID NO:48:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:48:

GGTACCTGCA TTTGCCAGCA C 21

( 2 ) INFORMATION FOR SEQ ID NO:49:

( i ) SEQUENCE CHARACTERISTICS:
   ( A ) LENGTH: 19 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:49:

GCTGCACTAT TGTCTTCTG 19

( 2 ) INFORMATION FOR SEQ ID NO:50:

( i ) SEQUENCE CHARACTERISTICS:
   ( A ) LENGTH: 19 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:50:

CAGCAACTGC TACAATCTG 19

( 2 ) INFORMATION FOR SEQ ID NO:51:

( i ) SEQUENCE CHARACTERISTICS:
   ( A ) LENGTH: 22 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:51:

GTGCAGGCTT ACAATGTACC AG 22

( 2 ) INFORMATION FOR SEQ ID NO:52:

( i ) SEQUENCE CHARACTERISTICS:
   ( A ) LENGTH: 24 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:52:

GCATTTACCT GGCTCCAATG ATTC 24

( 2 ) INFORMATION FOR SEQ ID NO:53:

( i ) SEQUENCE CHARACTERISTICS:

-continued

```
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

CCAATAGTAG  AAGGACTG                                                         1 8

( 2 ) INFORMATION FOR SEQ ID NO:54:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

CTTCAGATTG  GAAAGCGAGC  GGACGGAATC  ATTGATC                                  3 7

( 2 ) INFORMATION FOR SEQ ID NO:55:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

CTCAGCTTGA  AGAAGTGA                                                         1 8

( 2 ) INFORMATION FOR SEQ ID NO:56:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

GAAGCAGAGA  GGCTATTG                                                         1 8

( 2 ) INFORMATION FOR SEQ ID NO:57:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

GAAAATATAG  GGAAAATGT                                                        1 9
```